(12) United States Patent
Oraevsky

(10) Patent No.: US 12,379,492 B2
(45) Date of Patent: Aug. 5, 2025

(54) QUANTITATIVE IMAGING SYSTEM AND USES THEREOF

(71) Applicant: Alexander A. Oraevsky, Houston, TX (US)

(72) Inventor: Alexander A. Oraevsky, Houston, TX (US)

(73) Assignee: TomoWave Laboratories, Inc., Houston, TX (US)

( * ) Notice: Subject to any disclaimer, the term of this patent is extended or adjusted under 35 U.S.C. 154(b) by 1170 days.

(21) Appl. No.: 17/063,565

(22) Filed: Oct. 5, 2020

(65) Prior Publication Data

US 2021/0018620 A1 Jan. 21, 2021

Related U.S. Application Data

(63) Continuation-in-part of application No. PCT/US2019/025885, filed on Apr. 4, 2019.

(60) Provisional application No. 62/652,337, filed on Apr. 4, 2018.

(51) Int. Cl.
*A61B 5/00* (2006.01)
*A61B 8/08* (2006.01)
*G01S 7/521* (2006.01)
*G01S 15/89* (2006.01)

(52) U.S. Cl.
CPC ........ *G01S 15/8915* (2013.01); *A61B 8/0825* (2013.01); *G01S 7/521* (2013.01); *A61B 8/0858* (2013.01)

(58) Field of Classification Search
CPC . A61B 2576/00; A61B 5/0033; A61B 5/0073; A61B 5/0091; A61B 5/0095; A61B 8/08; A61B 8/0808; A61B 8/0825; A61B 8/0858; A61B 8/40; A61B 8/4272; A61B 8/4483; A61B 8/463; A61B 8/481; A61B 8/483; A61B 8/5223; A61B 8/5246; A61B 8/5261; G01S 15/8915; G01S 15/894; G01S 15/8965; G01S 15/8993; G01S 7/521

See application file for complete search history.

(56) References Cited

U.S. PATENT DOCUMENTS

2008/0037933 A1* 2/2008 Furman ............... G02B 6/14
                                                     385/31
2013/0190595 A1* 7/2013 Oraevsky ........... A61B 8/483
                                                    600/407

OTHER PUBLICATIONS

Beyatli et al., "Self-Q-switched Cr:LiCAF laser", J. Opt. Soc. Am. Apr. 2013 (Year: 2013).*

* cited by examiner

*Primary Examiner* — Christopher L Cook
(74) *Attorney, Agent, or Firm* — Benjamin Aaron Adler

(57) ABSTRACT

Provided herein are imaging systems such as a system for quantitative tomography and a laser optoacoustic ultrasonic imaging system assembly (LOUISA) for imaging a tissue region, for example, a breast, in a subject. Generally, the system components are a laser that emits instant pulses of laser light in a wavelength cycling mode, fiberoptic bundles or optical arc-shaped fiber bundles configured to deliver laser light, an imaging module with an imaging tank, an optoacoustic array(s) of ultrawide-band ultrasonic transducers and ultrasound array(s) of ultrasonic transducers and a coupling medium and an electronics subsystem. Also provided is a method for imaging quantitative functional parameters and/or molecular parameters and anatomical structures in a volumetric tissue region of interest, such as a breast, in a subject utilizing the system for quantitative tomography.

26 Claims, 14 Drawing Sheets

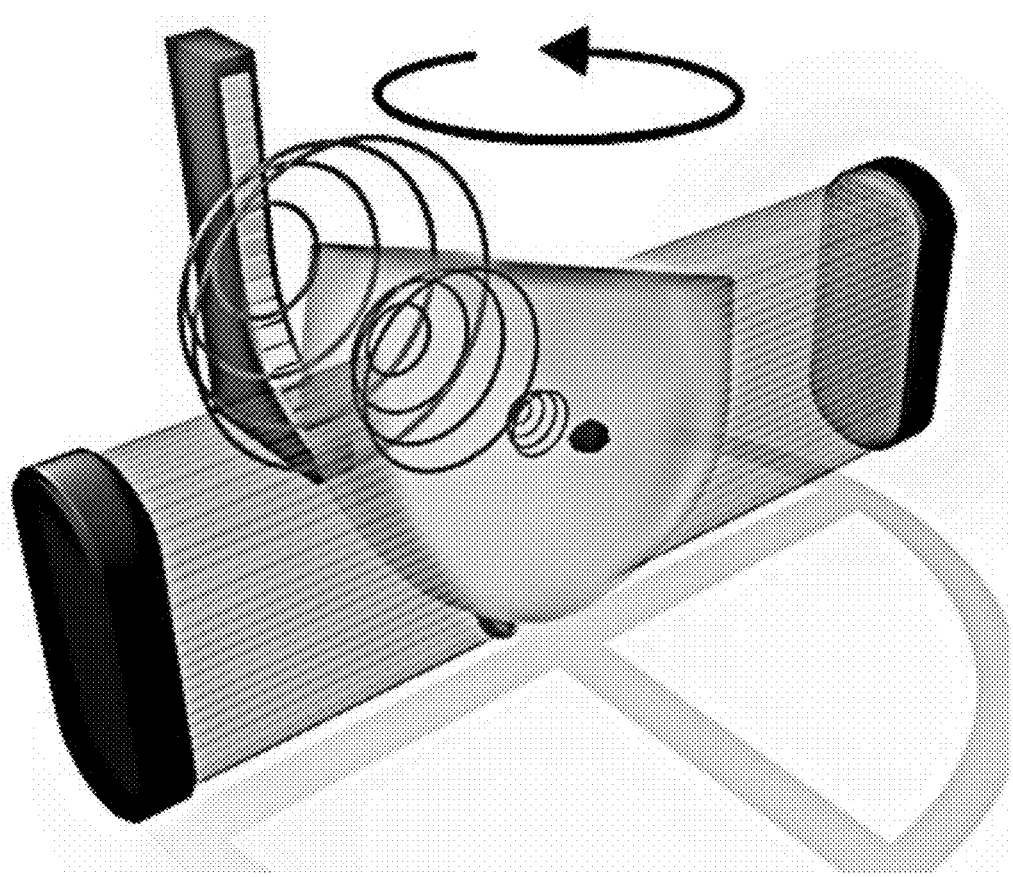
FIG. 1A
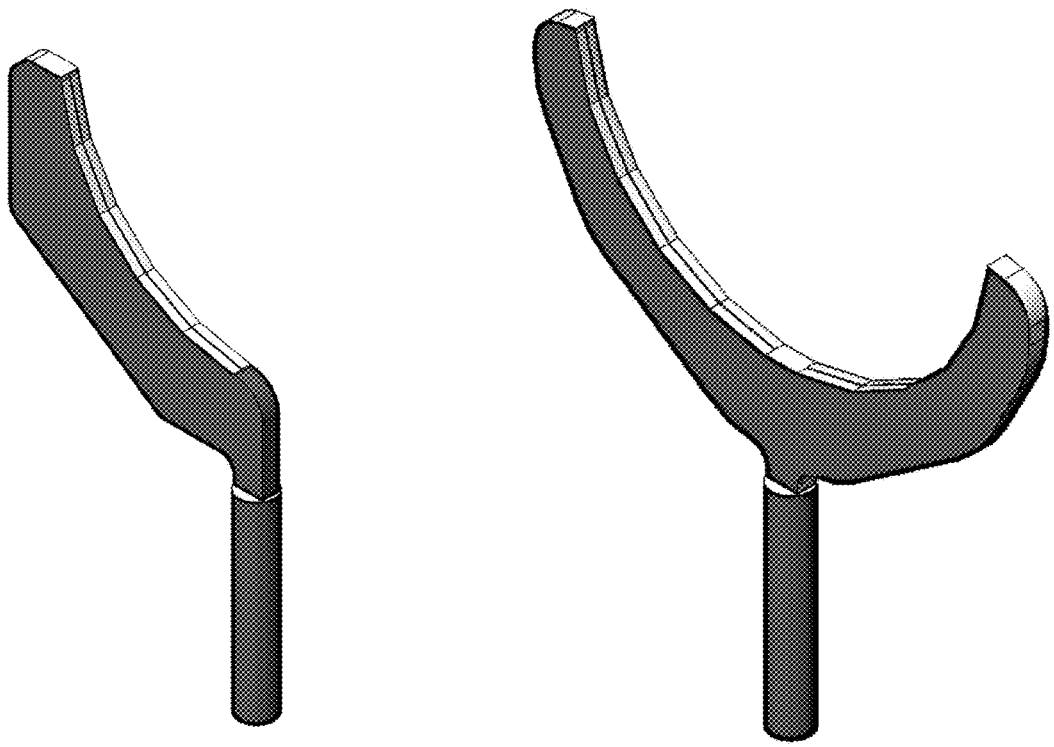
FIG. 1B
FIG. 1C

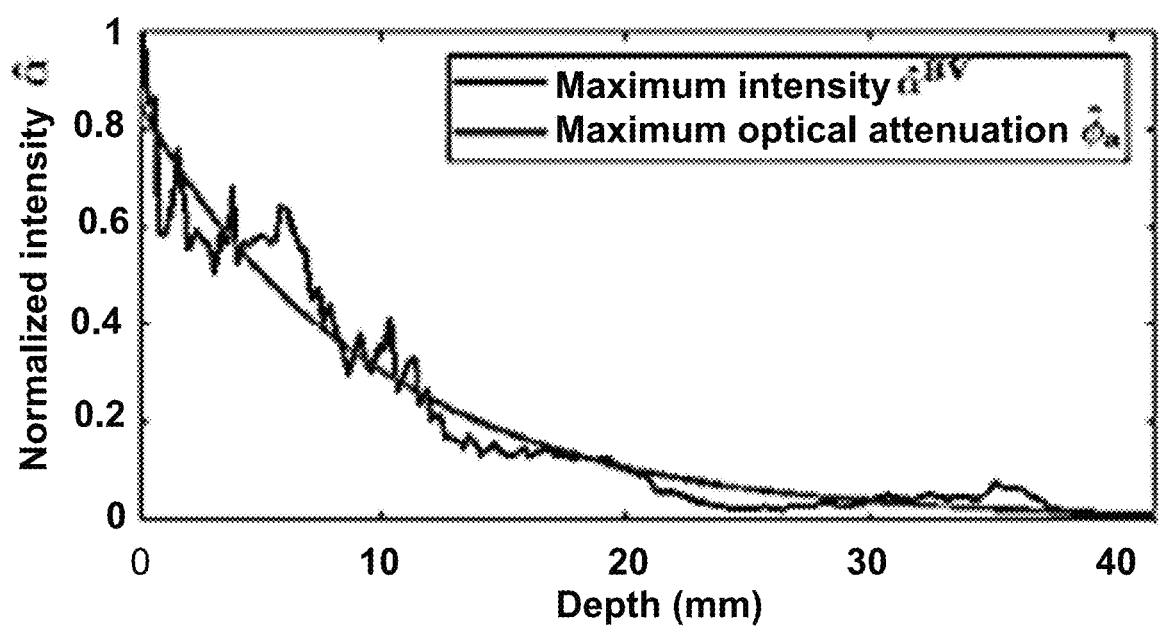
FIG. 9A
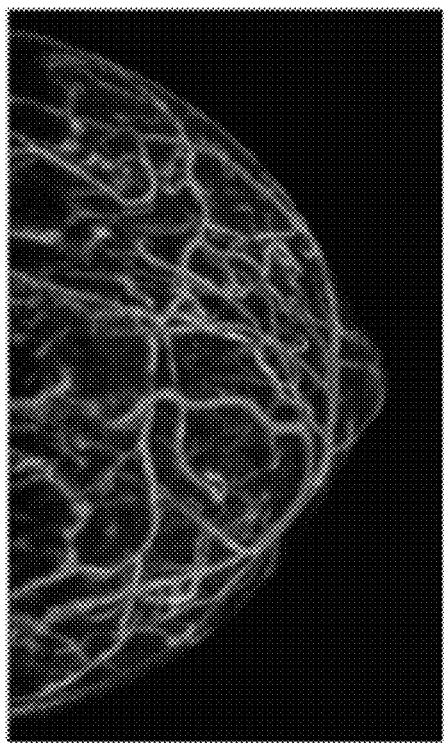
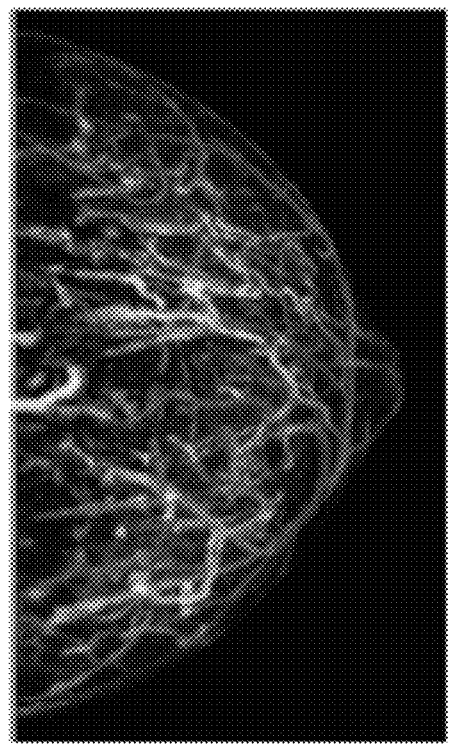
FIG. 9B	FIG. 9C

QUANTITATIVE IMAGING SYSTEM AND USES THEREOF

CROSS-REFERENCE TO RELATED APPLICATIONS

This application is a continuation-in-part of international application PCT/US2019/025885, filed Apr. 4, 2019, which claims benefit of priority under 35 U.S.C. § 119(e) of provisional application U.S. Ser. No. 62/652,337, filed Apr. 4, 2018, the entirety of which is hereby incorporated by reference.

FEDERAL FUNDING LEGEND

This invention was made with government support under Grant Number R01CA167446 awarded by the National Institutes of Health. The government has certain rights in the invention.

BACKGROUND OF THE INVENTION

Field of the Invention

The present invention relates to the field of biomedical imaging and tomography systems that can provide medical information about a volumetric region of interest of the body under examination. More specifically, the present invention provides a laser optoacoustic ultrasonic imaging system assembly (LOUISA) for quantitative three dimensional tomography of a tissue region of interest in a subject to obtain quantitative images of functional and molecular parameters within anatomical tissue structures.

Description of the Related Art

Aggressive cancer cannot develop into life-threatening disease without the support of nutrition and oxygen from the microvasculature, as discovered by Judah Folkman (1). The optical absorption spectra of oxygenated and deoxygenated hemoglobin in the human body are such that they allow selection of two near-infrared wavelengths that when used with optoacoustic tomographic imaging, can establish a contrast of oxyhemoglobin and deoxyhemoglobin useful in creation of functional imaging modalities (2). The distinction between the two oxygenation states of hemoglobin affords localization of arteries feeding the tumors and veins draining from the tumors. With this capability, a radiologist is expected to differentiate highly vascularized and hypoxic tissues of malignant tumor growth and to recommend biopsy with a greater level of confidence than presently expected when 7 to 8 out 10 biopsy procedures come with negative results (3). These optoacoustic images can improve sensitivity of detection and specificity of medical diagnostics compared with ultrasound alone by providing functional information of the total hemoglobin [tHb] and blood oxygen saturation [sO2] within tumors and displayed within morphological tissue structures of the breast (4).

Being motivated by a great medical need and a large market for improved breast imaging systems, a number of clinical prototype systems based on the principles of optoacoustic tomography have been developed since the beginning of the $21^{st}$ century (5-12) and all have reported sufficient technical capabilities in detection of breast cancer. However, the only system tested in statistically significant multicenter studies and reported clinical viability is Imagio (Seno Medical Instruments, San Antonio, TX) (3). This dual-modality optoacoustic/ultrasonic imaging system has an advantage of convenience and of real-time video frame rate capability associated with design based on a hand-held probe (13). However, the hand-held probe with its limited field of view provides 2D slices that can be interpreted only by highly trained radiologists, reduced lateral resolution and incomplete tomographic recovery of quantitative image brightness.

Therefore, there is a recognized need in the art for three-dimensional full view tomography systems that provide automatic screening of the full breast with quantitatively accurate and easily interpretable volumetric images. Particularly the prior art is deficient in a quantitative functional anatomical imaging system for breast screening with simultaneous diagnostics of cancerous tumors. More particularly, the invented design represents a platform technology of the quantitative optoacoustic imaging where functional and molecular images are displayed within anatomical tissue structures visualized by coregistered ultrasound images. The invented technology can be used in various clinical applications in detection of cancer (breast, brain, head & neck, testicular) and vascular abnormalities (stroke, hemorrhages, deep vein thrombosis) as well as in preclinical research using small animal models of human diseases. The present invention fulfills this long standing need and desire in the art.

SUMMARY OF THE INVENTION

The present invention is directed to a system for quantitative tomography. In the system a laser is configured to emit instant (about 1-100 nanosecond) pulses of laser light at wavelengths within a red to near-infrared spectral range where the laser is operable in a wavelength cycling mode. The wavelength cycling mode allows generation of different wavelengths with each next laser pulse, so that 2, 3, or more wavelengths can be emitted one after another and the cycle repeated. The wavelength cycling is important for coregistration of images in time and space, so that all voxels of coregistered images match even in a live tissue volume. Coregistered images can be compared quantitatively and derivative images such as functional and molecular images can be produced, and images of functional parameters such as total hemoglobin and blood oxygen saturation or images of molecular distributions can be displayed within anatomical tissue structures. In the system a fiberoptic bundle is configured to deliver the instant pulses of laser light to an entire tissue region of interest with maximum transmission. In order to achieve maximum transmission the input tip of the fiber bundle is hot-fused to convert circular shape of the optical fibers into hexagonal shape, which in turn eliminates spaces between fibers and tightly packs them in a high transmission optical illumination system.

In the system an imaging module comprises an imaging tank with a shape corresponding to the volumetric tissue region of interest. The most preferred geometry of the imaging module is a sphere or at least portion of the sphere that permits rigorous reconstruction of quantitative images. The imaging module is filled with optoacoustic coupling medium, enabling transmission and coupling of near infrared light and ultrasound waves without losses. The imaging module contains at least one optoacoustic array of ultrawideband ultrasonic transducers and at least one ultrasound array of ultrasonic transducers. The optoacoustic transducer array and the ultrasonic transducer array may be combined in one physical housing, and one and the same array of ultrawideband ultrasonic transducers can serve both purposes of acquisition of optoacoustic and ultrasonic images. In the system the optoacoustic array of ultrawide-band ultrasonic transducers is configured to detect ultrasonic signals within an ultrawide-band of ultrasonic frequencies from about 50 kHz to about 15 MHz generated in the tissue region of interest by the instant pulses of laser light. Capability to detect ultrawide band of ultrasonic frequencies is critically important for quantitative imaging that relies on detection of undistorted optoacoustic signals generated in tissues by instant laser pulses. Lower ultrasonic frequencies carry quantitative volumetric information from larger objects on the image (such as tumors) and higher frequencies provide sharp edges and high resolution of the quantitative images. The range of ultrawide band of ultrasonic frequencies can be adjusted for each specific medical application, organ or volumetric region of interest containing different types of tissues. For example, in case of deep imaging of a large organ such as breast, the range of ultrasonic frequencies can be reduced to 50 kHz-8 MHz without loss of resolution and medical viability. At least one ultrasound array of ultrasonic transducers is configured to transmit pulses of ultrasound into the tissue region and to detect ultrasonic signals reflected from or transmitted through the tissue region. The array of ultrawide band ultrasonic transducers that transmits ultrasound pulses upon application of electrical pulses and used for purposes of ultrasound imaging can be replaced with laser ultrasound array of polymer emitters with embedded strong optical absorbers. The advantage of laser ultrasound array compared with electrical ultrasound array is the capability to generate ultrawide-band ultrasound pulses to match ultrawide-band ultrasound frequency range of optoacoustic signals, and in turn enable volumetric ultrasound images.

In the system the optoacoustic array and the ultrasound transducer array are connected to a multichannel electronic data acquisition system (DAS). DAS comprises analog preamplifiers, analog-to-digital converters and digital data storage, and processing and transmission boards. The data acquisition system is controlled by a Field Programmable Gate Array microprocessor(s). A computer is in electronic communication with the multichannel electronic data acquisition system and comprises a multicore central processing unit (CPU) and a multicore graphics processing unit (GPU) and tangibly storing software configured to control said CPU and GPU for system control, signal processing, image reconstruction and image coregistration. A high-resolution display is connected electronically to the computer to present the reconstructed image to an operator of the system for quantitative tomography.

The present invention also is directed to a method for imaging (i) quantitative functional parameters such as total hemoglobin (tHb) and blood oxygen saturation (sO2) in a tissue region of interest in a subject and (ii) quantitative concentrations of optically absorbing molecules or nanoparticles. The tissue region is placed in the imaging tank of the system for quantitative tomography described herein and the optoacoustic array of ultrawide-band ultrasonic transducers and the ultrasound array of ultrasonic transducers are positioned inside the imaging tank. Wavelengths of laser light are selected within the red to near-infrared spectral range for delivery as instant pulses to the tissue region in the wavelength cycling mode and the cycling instant pulses of laser light in the selected range of wavelengths are delivered to the tissue region. For each selected wavelength signals within the ultrawide-band of ultrasonic frequencies generated within the tissue region are detected with the optoacoustic array and optoacoustic images from the detected signals are acquired for each selected wavelength and are coregistered. Images of quantitative functional parameters or molecular parameters are generated from the coregistered optoacoustic images and the generated quantitative images are displayed.

The present invention is directed to a related imaging method. The method further comprises transmitting to the tissue region pulses of ultrasound from the ultrasound array and detecting with the ultrasound array signals reflected from or transmitted through the tissue region. Speed of sound images based on a distribution of speed of sound within the tissue region and anatomical images of ultrasound reflection or attenuation from the detected ultrasonic signals are generated. The images of quantitative functional parameters or molecular parameters are coregistered with the anatomical structures and the coregistered images are displayed as an overlay of the images of quantitative or functional parameters with the anatomical images or speed of sound images. The present invention is directed to a method of further enhancing resolution and quantitative accuracy of the optoacoustic images and the ultrasound reflection or attenuation images via utilization of the speed of sound images. The present invention represents a system and a method directed to detection and diagnostics of cancer and vascular abnormalities from the quantitative functional parameters or molecular parameters displayed in the overlay within the anatomical tissue structures.

The present invention is directed further to a laser optoacoustic ultrasonic imaging system assembly (LOUISA) for imaging a breast in a subject. A laser is configured to emit instant pulses of laser light at wavelengths within a red to near-infrared spectral range, said laser operable in a wavelength cycling mode of two or three wavelengths within the spectral range. An optical arc-shaped fiber bundle is configured to rotate around the breast to deliver the instant pulses of laser light to an entire breast. An imaging tank with a spherical surface shape corresponding to the breast. An optically and acoustically transparent coupling liquid fills the imaging tank through which the instant pulses of laser light and the pulses of ultrasound are transmitted. One design uses an arc-shaped optoacoustic array of ultrawide-band ultrasonic transducers configured to detect ultrasonic signals within an ultrawide band of 50 kHz to 8 MHz generated in the breast by the instant pulses of laser light and at one arc-shaped ultrasound array of ultrasonic transducers configured to transmit pulses of ultrasound into the breast and to detect ultrasonic signals reflected from or transmitted through the breast. An alternative and preferred design of the breast imaging system uses one and the same array of ultrawide-band ultrasonic transducers for purposes of both, optoacoustic and ultrasound imaging. In order to use one array for both types of images, the array must be 1.5-dimensional or 2-dimensional and have no physical acoustic lens, while effects of focusing or reconstruction of 2D and 3D images can be achieved through microprocessor controlled beamforming and algorithms of image reconstruction implemented in the electronic data acquisition board and computer.

Electronic data acquisition boards in LOUISA comprise a multichannel electronic data acquisition system, a computer in electronic communication with the multichannel electronic data acquisition system and a high-resolution display electronically connected to the computer. The multichannel electronic data acquisition system comprises analog preamplifiers, analog-to-digital converters and digital data storage, and processing and transmission boards, said data acquisition system controlled by a Field Programmable Gate Array microprocessor(s). The computer comprises a multicore central processing unit (CPU) and a multicore graphics processing unit (GPU) and tangibly storing software configured to control said CPU and GPU for system control, signal processing, image reconstruction and image coregistration. The high-resolution display presents the reconstructed image of the breast to an operator of the LOUISA system.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A depicts a basic cartoon schematic of the full view 3D optoacoustic tomography and FIGS. 1B-1E illustrate the breast-scanning system Laser Optoacoustic Ultrasonic Imaging System Assembly (LOUISA). FIG. 1A shows rotating arc-shaped fiberoptic illuminators that illuminated the volumetric region of interest and thus, generated ultrasonic (optoacoustic) signals from the optical absorption by a tumor, which can then be detected by an independently rotating optoacoustic probe, which provides a comprehensive signal dataset for rigorous volumetric reconstruction. FIG. 1B is an optical fiber bundle with a single arc-shaped fiberoptic paddle (see 7, in FIG. 1C). FIG. 1C is an optical fiber bundle with two arc-shaped fiberoptic paddles. FIG. 1D shows an imaging module for scanning a large breast. The imaging module has an imaging module platform 1 positioned on the large motor stage 2 to rotate the imaging tank 3 containing concave arc shaped ultrasonic transducer array 4 (US probe) and a concave arc-shaped optoacoustic transducer array 5 (OA probe), around the breast. The imaging tank is filled with optoacoustic coupling medium where the breast is stabilized within the imaging module using a breast stabilizer (see FIG. 1E) that is a very thin optically and acoustically transparent plastic cup shaped with a spherical surface. The OA probe and the US probe are connected to the preamplifier boards 6 directly connected to the optoacoustic probe expanding the bandwidth of the optoacoustic transducers, optical arc-shaped fiber bundle (fiberoptic paddle) 7 to illuminate the breast with a homogeneous beam of light, this fiberoptic system may have one (see FIG. 1B), two (see FIG. 1C) or several arc-shaped fiberoptic paddles for faster illumination of the entire breast and a small motor 8 to rotate the arc-shaped fiberoptic paddle around the imaging bowl. FIG. 1E shows the breast stabilizer that molds the breast into a precise spherical shape.

FIG. 5A illustrates that the vein is brightly visible with illumination at 757 nm. FIG. 5B illustrates that the artery is brightly visible at 1064 nm. This is an example demonstrating capability of functional optoacoustic imaging.

FIG. 7A is a raw unprocessed image that shows only shallow blood vessels due to heterogeneous distribution of optical energy on the surface and through depth of the breast. FIG. 7B is an optoacoustic (OA) image processed by normalization (equalization) of the laser energy distribution on the surface of the breast that shows greater visibility of blood vessels images. FIG. 7C is an optoacoustic image processed by compensating for the effective optical attenuation as a function of depth that shows full depth of imaging in the breast. Simultaneously, this image becomes quantitative showing the optical absorption coefficient distribution independently on the distribution of the optical fluence.

FIG. 8A is the normalized intensity (brightness) of the optoacoustic image of the breast measured right under the skin shown as function of polar angle, θ. The values of θ from 0 to 90 point into the chest wall, so they are presented. The values of θ from 150 to 180 point to the nipple area with enhanced heterogeneous absorption, so they have been neglected. The values of θ from 90 to 150 point to the skin and were used to estimate incident optical fluence on the skin due to rotating fiberoptic bundle. The line extrapolating the experimentally measured values was used to normalize the optical fluence through entire breast surface. FIG. 8B shows maximum intensity projection image of a healthy breast vasculature with even optical fluence illumination.

FIGS. 9A-9C illustrates method to normalize the optical fluence through the depth of the breast displayed on an optoacoustic mage by compensating for the effective optical attenuation at each wavelength used in the cycle of 2 cycling wavelengths. FIG. 9A shows experimental curve of image intensity (brightness) measured from a 3D optoacoustic image of the breast acquired at the wavelength of 757 nm. The experimental curve shows the presence of background optical absorption by unresolved microvasculature and deviation from the background due to the presence of larger blood vessels. This type of measurement was only possible from the optoacoustic image acquired with ultrawide band ultrasonic transducers sensitive in the lower ultrasonic frequency range. The solid curve is an exponential curve showing the effective optical attenuation through the depth of the breast according to Beer-Lambert law. FIG. 9B is an optoacoustic MIP image processed by normalization (equalization) of the laser energy distribution on the surface of the breast, but not normalized by compensating for the effective optical attenuation through the depth of the breast. FIG. 9C is an optoacoustic MIP image processed by compensating for the effective optical attenuation as a function of depth that shows full depth of imaging in the breast.

FIG. 12A shows the patient platform in the vertical position. A patient approaches this platform, leans on the platform and the platform moves into the horizontal position. FIG. 12B shows the platform in the horizontal position. The patient does not need to move adjusting her position. The imaging module on a 3D translational stage will be brought in an optimal position for the breast exam without any need to adjust the patient position, making the exam comfortable and fast.

FIG. 14 (bottom panel of 3 images) shows that mouse vasculature and organs become visible through the entire body after the proprietary fluence normalization.

DETAILED DESCRIPTION OF THE INVENTION

Figure 1D:
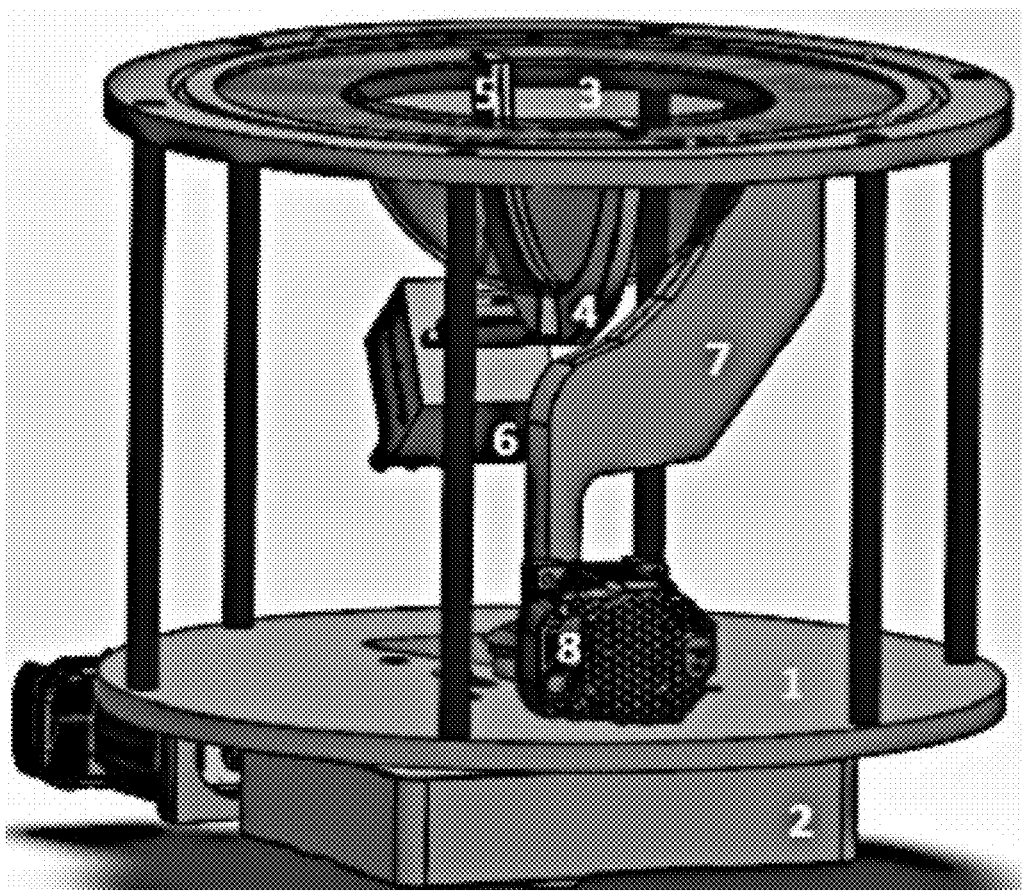
Figure 1E:
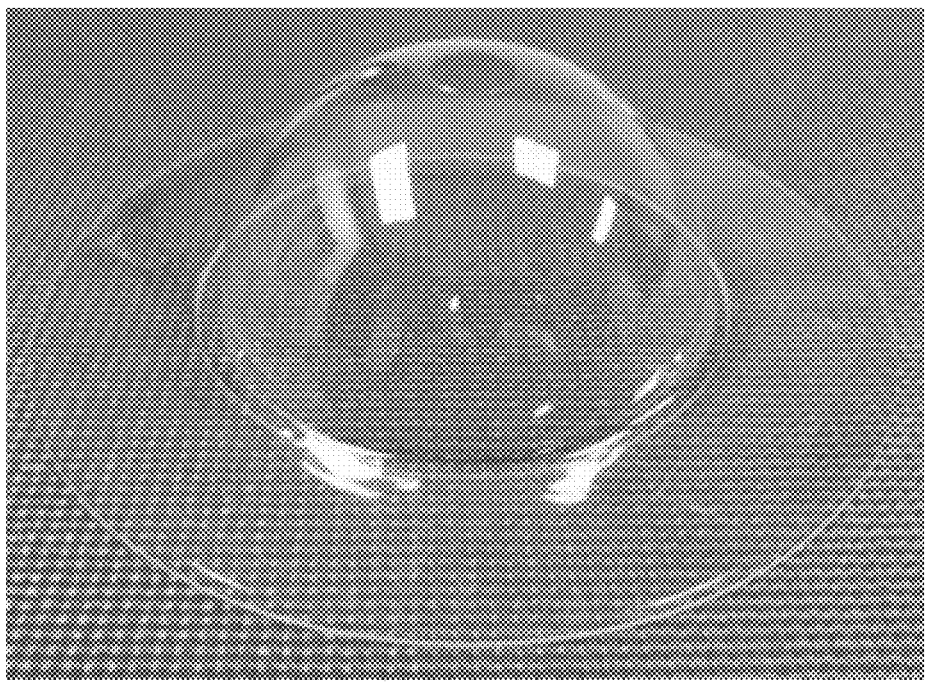

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +1-5-10% of the recited value) that one of ordinary skill in the art would consider equivalent to the recited value (e.g., having the same function or result). In some instances, the term "about" may include numerical values that are rounded to the nearest significant figure.

As used herein, the terms "small animal" or "small laboratory animal" or the plurals thereof are interchangeable and refer to, but are not limited to, a mouse, a rat or a guinea pig, preferably a mouse.

In one embodiment of the present invention there is provided a system for quantitative tomography comprising a laser configured to emit instant pulses of laser light at wavelengths within a red to near-infrared spectral range, said laser operable in a wavelength cycling mode; an fiberoptic bundle configured to deliver the instant pulses of laser light to an entire tissue region of interest with maximum transmission;

an imaging module comprising an imaging tank with a shape corresponding to the tissue region of interest; at least one optoacoustic array of ultrawide-band ultrasonic transducers configured to detect ultrasonic signals within an ultrawide band of ultrasonic frequencies generated in the tissue region of interest by the instant pulses of laser light; at least one ultrasound array of ultrasonic transducers configured to transmit pulses of ultrasound into the tissue region and to detect ultrasonic signals reflected from or transmitted through the tissue region; and a coupling medium that fills the imaging tank and through which the instant pulses of laser light and the pulses of ultrasound are transmitted; a multichannel electronic data acquisition system comprising analog preamplifiers, analog-to-digital converters and digital data storage, and processing and transmission boards, the data acquisition system controlled by a Field Programmable Gate Array microprocessor(s); a computer in electronic communication with the multichannel electronic data acquisition system and comprising a multicore central processing unit (CPU) and a multicore graphics processing unit (GPU) and tangibly storing software configured to control said CPU and GPU for system control, signal processing, image reconstruction and image coregistration; and a high-resolution display electronically connected to the computer to present the reconstructed image to an operator of the system for quantitative tomography.

In this embodiment the red and near-infrared spectral range of wavelengths is about 650 nm to about 1250 nm.

Also the wavelength cycling mode may two or three wavelengths within the red to near-infrared spectral range. In an aspect of this embodiment the two cycling wavelengths are 757 nm and 850 nm. In this aspect the laser may be a Nd:YAG pumped OPO laser for quantitative molecular imaging. In another aspect the three cycling wavelengths are 757 nm, 800 nm and 850 nm or 757 nm, 800 nm and 1064 nm. In this aspect the laser may be a Cr:LICAF laser for quantitative functional imaging, which is a preferred laser, which can cover the full range of wavelengths required for functional imaging from 757 nm to 850 nm. In addition the maximum transmission of the instant pulses of laser light may be performed with hot fused input tip that makes honeycomb shape of fibers in the bundle.

Also in this embodiment the ultrawide-band ultrasonic transducers in the array may detect ultrasonic signals within an ultrawide band of 50 kHz to 6 MHz. In an aspect the optoacoustic array of ultrawide ultrasonic transducers and the ultrasound array of ultrasonic transducers are combined into one array. In addition the wherein the imaging tank in the imaging module has a spherical surface shape or a cylindrical shape. An example of the tissue region of interest is a region of breast tissue.

Furthermore in this embodiment the software enables processor-executable instructions for signal processing and image processing to produce images of quantitative molecular concentrations or functional parameters within the tissue region of interest or anatomical structures. In aspects thereof the instructions may be configured to restore original profiles of an optoacoustic signal generated in the tissue region by the instant laser pulses using deconvolution of acousto-electrical and spatial impulse response functions of the ultrawide-band ultrasonic transducer from the detected optoacoustic signals; reconstruct 3D optoacoustic tomography images of the tissue region via rigorous direct algorithms or iterative algorithms utilizing complete data sets acquired in full view geometry; normalize distribution of incident optical fluence on a surface of the tissue region by equalizing image brightness of all surface voxels; normalize distribution of the incident optical fluence through the entire tissue region by compensating for effective optical attenuation; display images of an optical absorption coefficient after normalization of the incident optical fluence through the tissue region on optoacoustic images of optical energy absorbed in the tissue region; produce coregistered optoacoustic images acquired at two or three cycling laser wavelengths to obtain quantitative functional or molecular images; and acquire images of speed of sound distribution within the tissue region that are used to improve contrast and resolution of coregistered optoacoustic images or images of ultrasound reflection and attenuation.

In a related embodiment of the present invention there is provided a laser optoacoustic ultrasonic imaging system assembly (LOUISA) for imaging a breast in a subject, comprising a laser configured to emit instant pulses of laser light at wavelengths within a red to near-infrared spectral range, said laser operable in a wavelength cycling mode of two or three wavelengths within the spectral range; an optical arc-shaped fiber bundle configured to rotate around the breast to deliver the instant pulses of laser light to an entire breast; an imaging tank with a spherical surface shape corresponding to the breast; at least one arc-shaped optoacoustic array of ultrawide-band ultrasonic transducers configured to detect ultrasonic signals within an ultrawide band of 50 kHz to 6 MHz generated in the breast by the instant pulses of laser light; at least one arc-shaped ultrasound array of ultrasonic transducers configured to transmit pulses of ultrasound into the breast and to detect ultrasonic signals reflected from or transmitted through the breast; an optically and acoustically transparent coupling medium that fills the imaging tank and through which the instant pulses of laser light and the pulses of ultrasound are transmitted; and an electronic subsystem comprising a multichannel electronic data acquisition system comprising analog preamplifiers, analog-to-digital converters and digital data storage, and processing and transmission boards, said data acquisition system controlled by a Field Programmable Gate Array microprocessor(s); a computer in electronic communication with the multichannel electronic data acquisition system and comprising a multicore central processing unit (CPU) and a multicore graphics processing unit (GPU) and tangibly storing software configured to control said CPU and GPU for system control, signal processing, image reconstruction and image coregistration; and a high-resolution display electronically connected to the computer to present the reconstructed image of the breast to an operator of the LOUISA system.

In this embodiment the two cycling wavelengths may be 757 nm and 850 nm. Also in this embodiment the three cycling wavelengths are 757 nm, 800 nm and 850 nm or 757 nm, 800 nm and 1064 nm. In addition the optoacoustic array of ultrawide ultrasonic transducers and the ultrasound array of ultrasonic transducers may be combined into one array. Furthermore the arc-shaped fiber bundle, the arc-shaped optoacoustic array and the arc-shaped ultrasound array are configured to independently rotate around the breast for illumination of the entire breast for each position of the optoacoustic array and the ultrasound array.

In another embodiment of the present invention there is provided a method for imaging quantitative or functional parameters in a tissue region of interest in a subject comprising the steps of placing the tissue region in the imaging tank of the system for quantitative tomography as described supra; positioning the optoacoustic array of ultrawide-band ultrasonic transducers and the ultrasound array of ultrasonic transducers inside the imaging tank; selecting wavelengths of laser light within the red to near-infrared spectral range for delivery as instant pulses to the tissue region in the wavelength cycling mode; delivering to the tissue volume the cycling instant pulses of laser light at the selected wavelength; detecting with the optoacoustic array for each selected wavelength signals within the ultrawide-band of ultrasonic frequencies generated within the tissue region; acquiring optoacoustic images from the detected signals for each selected wavelength; coregistering the optoacoustic images; generating images of quantitative functional parameters or molecular parameters from the coregistered optoacoustic images; and displaying the generated quantitative images.

Further to this embodiment the method comprises transmitting to the tissue region pulses of ultrasound from the ultrasound array; detecting with the ultrasound array signals reflected from or transmitted through the tissue region; generating speed of sound images based on a distribution of speed of sound within the tissue region; generating anatomical images of ultrasound reflection or attenuation from the detected ultrasonic signals; coregistering the images of quantitative functional parameter or molecular parameters within the anatomical structures; and displaying the coregistered images as an overlay of the images of quantitative or functional parameters with the anatomical images or speed of sound images. In another further embodiment the method comprises enhancing the optoacoustic images and the ultrasound reflection or attenuation images via the speed of sound images. In yet another further embodiment the method comprises diagnosing a cancer from the functional parameters or molecular parameters and the anatomical images displayed in the overlay. An example of a cancer is breast cancer.

In all embodiments detecting the signals generated at each selected wavelength may occur simultaneously. Also in all embodiments the quantitative functional parameter may comprise concentration of a protein, of a protein receptor or of a molecule associated with a breast cancer or a combination thereof. In addition the molecular parameter may be [tHb] or [sO2] or a combination thereof.

In one aspect of all embodiments the tissue region of interest may be spherically shaped and the transducer arrays are arc-shaped, the transducer arrays rotate around the region of interest by a computer-controlled motor. Also, for a spherically shaped tissue region of interest, a fiber bundle rotates around the region of interest independently on rotating transducer arrays, so that full illumination of the tissue region of interest is obtained for each position of the transducer arrays during the scan.

In another aspect of all embodiments the tissue region of interest may be cylindrically shaped and the transducer arrays may be arc-shaped or full ring shaped and translate along the region of interest by a computer controlled motor. Also for a cylindrically shaped tissue region of interest, a fiber bundle translates along the axis of the cylinder along with the transducer arrays.

In yet another embodiment of the present invention there is provided a system for quantitative tomography, comprising a laser configured to emit instant pulses of laser light at wavelengths within a red to near-infrared spectral range, where the laser is operable in a wavelength cycling mode; an fiberoptic bundle having a hot-fused input tip for maximum optical transmission that is configured to deliver the instant pulses of laser light to an entire volumetric tissue region of interest; an imaging module comprising an imaging tank shaped to accommodate a shape of the volumetric tissue region of interest; at least one optoacoustic array of ultrawide-band ultrasonic transducers configured to detect ultrasonic signals within an ultrawide band of ultrasonic frequencies generated in the volumetric tissue region of interest by the instant pulses of laser light; at least one ultrasound array of ultrasonic transducers configured to transmit pulses of ultrasound into the volumetric tissue region of interest and to detect ultrasonic signals reflected from or transmitted through the volumetric tissue region of interest; and a coupling medium that fills the imaging tank and through which the instant pulses of laser light and the pulses of ultrasound are transmitted; a multichannel electronic data acquisition system comprising analog preamplifiers, analog-to-digital converters and digital data storage, and processing and transmission boards, where the data acquisition system is controlled by a Field Programmable Gate Array microprocessor(s); a computer in electronic communication with the multichannel electronic data acquisition system and comprising a multicore central processing unit (CPU) and a multicore graphics processing unit (GPU) and tangibly storing software configured to control said CPU and GPU for system control, signal processing, image reconstruction and image coregistration of optoacoustic and ultrasonic images; and a high-resolution display electronically connected to the computer to present the reconstructed image to an operator of the system for quantitative tomography.

In this embodiment the red and near-infrared spectral range of wavelengths may be about 650 nm to about 1250 nm. Also in this embodiment the laser may be a Cr:LICAF laser crystal. In addition the wavelength cycling mode may be two or three wavelengths within the red to near-infrared spectral range. In one aspect, the two cycling wavelengths are 757 nm and 850 nm. In another aspect, the three cycling wavelengths are 757 nm, 800 nm and 850 nm or 757 nm, 800 nm and 1064 nm. Furthermore, the imaging tank in the imaging module may have a spherical surface shape or a cylindrical surface shape. Further still the volumetric tissue region of interest may be a human breast, a human head or a small animal.

Also in this embodiment the ultrawide-band ultrasonic transducers in the array may detect ultrasonic signals within an ultrawide band of 50 kHz to 6 MHz. In addition the ultrasound array of ultrasonic transducers may be a laser ultrasound array comprising polymers with high thermal expansion and filled with strongly optically absorbing materials. Furthermore, the ultrasound array of ultrasonic transducers may be a laser ultrasound array comprising polymers with high thermal expansion and filled with strongly optically absorbing materials.

In addition in this embodiment the software may enables processor-executable instructions for signal processing and image reconstruction and post-processing to produce images of quantitative molecular concentrations or functional parameters within the volumetric tissue region of interest, where the instructions are configured to a) produce coregistered optoacoustic images acquired at at least two cycling laser wavelengths to obtain quantitative functional or molecular images; b) for each image acquired at each wavelength in the cycle, restore original profiles of an optoacoustic signals generated in the volumetric tissue region by the instant laser pulses using deconvolution of acousto-electrical and spatial impulse response functions of the ultrawide-band ultrasonic transducer from the detected optoacoustic signals; c) for each image acquired at each wavelength in the cycle, reconstruct 3D optoacoustic tomography images of the volumetric tissue region via rigorous direct algorithms or iterative algorithms utilizing complete data sets acquired in full view geometry; d) for each image acquired at each wavelength in the cycle, normalize distribution of incident optical fluence on a surface of the volumetric tissue region by equalizing image brightness of all surface voxels with equal optical absorption; e) for each image acquired at each wavelength in the cycle, normalize distribution of the optical fluence as a function of depth through the entire tissue region by compensating for effective optical attenuation; f) for each image acquired at each wavelength in the cycle, produce and display images of an optical absorption coefficient after normalization of the optical fluence through the volumetric tissue region on optoacoustic images of the absorbed optical energy in the tissue region; g) use all coregistered images acquired at the at least two wavelengths in the cycle to produce a derivative image of quantitative molecular concentrations or functional parameters measured in the volumetric tissue region of interest.

Further to this embodiment the instructions may be further configured to transmit to the tissue region pulses of ultrasound from the ultrasound array; detect with the ultrasound array signals reflected from or transmitted through the tissue region; generate speed of sound images based on a distribution of speed of sound within the tissue region; generate anatomical images of ultrasound reflection or attenuation from the detected ultrasonic signals; coregister the anatomical images of ultrasound reflection, attenuation or speed of sound with quantitative functional or molecular images; and display the coregistered images as an overlay of the images of quantitative functional parameters within the anatomical tissue structures or an overlay of the quantitative functional and molecular images and speed of sound images.

In a related embodiment there is provided a laser optoacoustic ultrasonic imaging system assembly (LOUISA) for imaging a breast in a subject, comprising a pulsed laser configured to emit instant pulses of laser light at wavelengths within a red to near-infrared spectral range, where the laser is operable in a wavelength cycling mode of two or three wavelengths within the spectral range; an optical arc-shaped fiber bundle configured to rotate around the breast in steps to deliver the instant pulses of laser light at each step to the entire breast; an imaging tank with a spherical surface shape corresponding to the breast; at least one arc-shaped optoacoustic 1.5D or 2D array of ultrawideband ultrasonic transducers configured to detect ultrasonic signals within an ultrawide band of at least 50 kHz to at least 6 MHz generated in the breast by the instant pulses of laser light; at least one arc-shaped ultrasound 1.5D or 2D array of ultrasonic transducers configured to transmit pulses of ultrasound into the breast and to detect ultrasonic signals reflected from or transmitted through the breast, where the ultrasound array optionally is combined with the optoacoustic 1.5D or 2D array in one housing or is one array with the optoacoustic 1.5D or 2D array; an optically and acoustically transparent coupling medium that fills the imaging tank and through which the instant pulses of laser light and the pulses of ultrasound are transmitted; and an electronic subsystem comprising a multichannel electronic data acquisition system comprising analog preamplifiers, analog-to-digital converters and digital data storage, and processing and transmission boards, said data acquisition system controlled by a Field Programmable Gate Array microprocessor(s); a computer in electronic communication with the multichannel electronic data acquisition system and comprising a multicore central processing unit (CPU) and a multicore graphics processing unit (GPU) and tangibly storing software configured to control said CPU and GPU for system control, signal processing, image reconstruction and image coregistration; a software for system control, for signal processing to restore intrinsic signals by deconvolution of transducer impulse response, for image processing to normalize optical fluence on the surface and through the volume of the breast to enable quantitative functional and molecular images, for optoacoustic and ultrasonic image coregistration to display functional and molecular parameters within anatomical tissue structures; and a high-resolution display electronically connected to the computer to present the reconstructed image of the breast to an operator of the LOUISA system.

In this embodiment the two cycling wavelengths may be 757±5 nm and 850±10 nm. Also in this embodiment the three cycling wavelengths may be 757±5 nm, 800±5 nm and 850±10 nm or 757±5 nm, 800±5 nm and 1064±10 nm. In addition the optoacoustic array of ultrawide ultrasonic transducers and the ultrasound array of ultrasonic transducers may be combined into one array. Furthermore the arc-shaped fiber bundle, the arc-shaped optoacoustic array and the arc-shaped ultrasound array may be configured to independently rotate around the breast for illumination of the entire breast for each position of the optoacoustic array and the ultrasound array. Further still a patient examination may be made on a platform that moves from a vertical position to a horizontal position, and an imaging module is placed on a computer controlled three-dimensional translation stage, enabling a patient breast scan without patient movement on the platform.

In yet another embodiment of the present invention there is provided a method for imaging quantitative or functional parameters in a volumetric tissue region of interest in a subject with enhanced resolution and accuracy using image of the speed of sound, comprising the steps of placing the volumetric tissue region in the imaging tank of the system for quantitative tomography as described supra; generating images of quantitative functional parameters or molecular parameters from the coregistered optoacoustic images; acquiring images of speed of sound distribution within the tissue region; using images of the speed of sound to improve contrast and resolution of coregistered optoacoustic images or quantitative functional and molecular images; and displaying the generated images with enhanced resolution and quantitative accuracy.

Further to this embodiment the method may comprise enhancing the resolution of ultrasound reflection or attenuation images using maps of the speed of sound images. In another further embodiment the method may comprise detecting at least one cancerous tumor and differentiating it from a noncancerous tumor using coregistered images of the quantitative functional parameters or the molecular parameters displayed within anatomical structures in the overlay of optoacoustic and ultrasonic images. In an aspect of this further embodiment the cancerous tumor is a cancerous breast tumor.

In all embodiments acquiring ultrasound images occurs between acquiring optoacoustic images at cycling wavelengths. Also in all embodiments the quantitative functional parameter may comprise a concentration of a protein, of a protein receptor or of a molecule associated with a cancer or a combination thereof. In addition the functional parameter may be total hemoglobin [tHb] or blood oxygen saturation [sO2] or a combination thereof.

A full view three-dimensional (3D) volumetric medical imaging system was developed in response to demands from diagnostic radiologists for a quantitative optoacoustic tomography (QOAT) system combined with ultrasound tomography, such QOAT system is capable of providing quantitative molecular and functional information within specific anatomical structures such as tumors and their environment. One of many important applications of such a system is in the detection and diagnosis of cancer. Thus, the present invention provides a Laser Optoacoustic Ultrasonic Imaging System Assembly (LOUISA) for the detection and diagnosis of breast cancer.

Technical features of this system help to improve low detection sensitivity of Xray-based modalities of mammography and tomosynthesis in the dense and heterogeneous breast and low diagnostic specificity of magnetic resonance imaging. We teach that coregistration of quantitatively accurate molecular images of the breast showing functional parameters of the total hemoglobin [tHb] and blood oxygen saturation [sO2] within the breast morphological structures including tumors and their surroundings will provide a clinically-viable solution for the breast cancer care. Quantitative molecular imaging in LOUISA is enabled by the unique hardware features and software methods and algorithms of the optoacoustic subsystem described below. Anatomical imaging of specific structures within the tissue region of interest (ROI), such as tumors, is enabled by hardware features and software methods and algorithms of the ultrasound subsystem described below. What makes this system not only clinically viable but also practical is the new signal acquisition and scan design, which enable rapid volumetric 3D scanning of the full ROI adding the fourth dimension of time to the system 3D capability. Ultimately, the system is capable of time-resolved 3D imaging, not only space resolved imaging.

System Overview

The Quantitative Optoacoustic Tomography (QOAT) system has six main components that enable its operation and novel features and abilities:

1. A pulsed laser emitting instant pulses of optical energy in the red and near-infrared spectral range with wavelength cycling capability. "Instant pulses" as used herein means that the duration of these laser pulses is much shorter than the time it takes for acoustic wave to propagate with the speed of sound through a voxel to be resolved on optoacoustic images. For example, if a desirable image resolution, i.e. voxel size is 0.15 mm, then considering the speed of sound is 1.5 mm/microsec, the time it takes for an acoustic wave to propagate through this voxel is 0.1 microsec. "Much shorter" means at least 3 times shorter. Therefore, for this specific example laser pulses will be shorter than 30 nsec. Too short pulses are also not acceptable, because they can damage optical elements of the system, first of all, the fiberoptic light delivery subsystem.

The red and near-infrared spectral range is the range of wavelengths from 650 nm to 1250 nm. This wavelength range is important for deep penetration of the optical energy into the biological tissue and, simultaneously, for strong optical absorption by medically important molecules such as hemoglobin, oxyhemoglobin, lipids, water and exogenous contrast agents used in medical diagnostics and therapy. The wavelength cycling capability means that the emitted wavelength is changing with every laser pulse. The optimum number of wavelengths selected for quantitative functional imaging is 2, which corresponds to the two unknown concentrations of molecules or two unknown functional parameters.

If the molecules of interest are hemoglobin and oxyhemoglobin, the images that display the functional parameters of the total hemoglobin [tHb] and blood oxygen saturation [sO2] are called functional images. These images can be calculated based on optoacoustic images obtained at two wavelengths, one of which matching a peak optical absorption of hemoglobin, e.g. 757 nm, and the other matching a peak of optical absorption in oxyhemoglobin, e.g. 850 nm. Two wavelengths are the minimum necessary to measure and to display concentration of an exogenous contrast agent molecule on a background of endogenous molecules of tissue. In this case one wavelength is selected in a peak of the optical absorption of the exogenous molecule of interest and the second wavelength is selected outside of the optical absorption peak of this molecule of interest.

To increase accuracy of quantitative information from molecular or functional images 3 cycling wavelengths can be used. For example, the third wavelength of 800 nm can be used for functional imaging of [tHb] and [sO2]. This third wavelength can be used for normalization of functional images because it corresponds to the isosbestic point in the optical absorption spectrum where absorption coefficients of hemoglobin and oxyhemoglobin are equal. The preferred number of wavelengths for quantitative molecular imaging of exogenous contrast agents (such as dyes or nanoparticles) is 3, which corresponds to two unknown molecular concentrations and an isosbestic point of equal optical absorption at which the images can be normalized. More than 3 wavelengths in the cycle are not practical in medical imaging as the total image acquisition time to obtain quantitative images must be as short as possible.

Wavelength cycling is critically important for coregistration of optoacoustic images that enables generation of molecular (functional) images through mathematical operations such as summation, subtraction and division. Only coregistered images can undergo mathematical operations, otherwise the resulting image will have a huge level of errors. The images are coregistered when each voxel of one image is in the same location (coordinates) as on the second image, which can be achieved only if live tissues do not move during the time when both images are acquired. Therefore, two images must be acquired simultaneously or as soon as possible one after the other in order to achieve coregistration. The desirable repetition rate of laser pulses is from 10 Hz to 50 Hz, which allows 100 msec to 20 msec time delay between images acquired at two different wavelengths. It is possible, however, to reduce the time delay between acquisitions of two images to a minimum, which is equal to the time of ultrasound propagation from the farthest voxel in ROI to the ultrasound transducers in the detector array (about 0.15 msec). This ultimate coregistration can be achieved with a dual laser design, which allows triggering of two cycling wavelength emissions with any predetermined delay. This, in turn, allows us to record two sequential optoacoustic signals obtained at two cycling wavelengths as one signal recorded by the Data Acquisition System with positions of the first sample in each optoacoustic signal accurately defined by the synchronization trigger.

2. Fiberoptic light delivery (FLD) subsystem. The fiberoptic bundle has a circular input to match the shape of the incident laser beam. The fibers in the tip are hot-fused to a honeycomb shape. The hexagonal shape of fibers in the bundle allow minimizing losses of light between the fibers and achieving maximum transmission of light to the output (up to 85%). The output is shaped according to the shape of the tissue ROI. Since most RIO of human organs have either spherical or cylindrical shape, the most beneficial shape of the fiberoptic output is an arc. An arc can be well approximated with a number of flat lines placed in an arc-shaped pattern. Multiple arc-shaped fiberoptic bundles can be used to increase the portion of ROI that is illuminated simultaneously by the same laser pulse. For example, the breast is an ROI for diagnostic imaging of breast cancer. Since the natural shape of the female breast is a hemisphere, the design of the FLD subsystem is a 90 deg arc or multiple arcs emanating from one center like petals of a flower (FIGS. 1A-1C). For other organs and ROIs such as neck, arms, legs, fingers the FLD output is still shaped as an arc, and multiple arcs of fibers can be shaped as cylindrical surfaces. The FLD subsystem is placed on a computer-controlled motor, so it can be rotated or translated to illuminate the entire ROI (FIG. 1D).

3. An imaging module with two probes represented by arrays of ultrasonic transducers sensitive to transient changes in pressure. The first probe is optoacoustic (OA), represented by an arc-shaped array of ultrawide-band ultrasonic transducers (UBT) operating in receive mode. The second probe is ultrasonic (US) represented by an arc-shaped array of ultrasonic transducers operating in transmit and receive modes. The arc shape of the probes can be represented by a number of flat lines placed along the arc. The arc shape of the probes allows significant increase of the acoustic aperture with small physical dimensions and in turn, enables high lateral resolution of images.

Both probes are placed in an optically transparent tank that in turn is connected to a computer-controlled motor (independently from the motor used for rotation or translation of the FLD subsystem), which can rotate around the spherically shaped tissue ROI or translate along the axis of symmetry of cylindrically shaped tissue ROI. Rotating and translating the probes around the tissue ROI enables collection of complete data sets for full view imaging and, in turn, reconstruction of quantitative tomographic images. Independence from the FLD subsystem motor and imaging tank motor enable complete illumination of full tissue ROI for each position of the probes. With this complete illumination of a full large organ is achieved with a less expensive laser having smaller pulsed energy, which makes the QOAT system more practical.

Alternatively, OA and US probes may be combined into one 1.5D or 2D probe, which serves purposes of both molecular imaging and anatomical imaging, which makes the QOAT system less expensive and more compact. Moreover, the goal of coregistration of molecular (optoacoustic) images with anatomical (ultrasound) images is achieved easier and naturally when the OA and US probes are combined into one. The probe may be either a linear array of transducers or a two-dimensional matrix of ultrasonic transducers. A two-dimensional matrix of ultrasonic transducers is the most beneficial for the QOAT system, as it enables flexible steering of the probe directivity, avoids the need for an acoustic lens, increases the probe sensitivity, permits reconstruction of 3D images with video rate, reduces the total time of scanning of a large tissue ROI.

The materials for the transducers in the probes are selected from those that allow design of ultrawide-band ultrasonic transducers, which is critically important for QOAT system. Without UBT the detected optoacoustic signals are significantly distorted which in turn results in much lower accuracy of quantitative information in molecular and functional images. Examples of transducer materials to design and to fabricate ultrawide-band ultrasonic transducers include, but are not limited to, single crystal piezoelectric composites such as PZT and PMN-PT. Capacitive micromachined ultrasonic transducers, cMUT, are also good candidates for design of UBT arrays. However, the most sensitive UBT arrays with the widest band of detectable ultrasonic frequencies extending in both, high and low frequency ranges were designed and fabricated from piezoelectric micromachined ultrasonic transducers, pMUT, which can provide the widest ultrawide band of detected ultrasound frequencies from 50 kHz to 15 MHz and in turn, optoacoustic images with highest quantitative accuracy, highest contrast and simultaneously with highest resolution. Optical detectors of transient ultrasonic waves also can be used as ultrawide-band ultrasonic transducers. The most promising designs of optical UBT are based on Fabry-Perot etalons that measure tissue displacement and balanced photodiode arrays that measure laser beam deflection angle.

4. A multichannel electronic Data Acquisition System (DAS) with low-noise analog preamplifiers, analog-to-digital converters and digital data storage, processing and transmission boards controlled by Field Programmable Gate Array microprocessors and rapid data transmission to a computer through a fast data ports such as USB3 or PCI express. Important features of the DAS are (i) high dynamic range (at least 14 Bits) enabling detection of strong signals from the tissue ROI surface and simultaneously weak signals from the depth of tissue, (ii) high sampling rate (at least 30 MHz) enabling accurate digitization of analog signals and (iii) long detectable signal length (at least 8000 samples) enabling the novel design of detecting two optoacoustic signals simultaneously as one signal thus reducing the time of image acquisition and providing conditions for perfect coregistration.

5. Computer with a processor, memory and at least one network connection and with software for the system control, data post-processing and image reconstruction, image conversion, image coregistration and image post-processing. The signal processing and image processing in the QOAT system is a critically important novelty of the system design, which utilizes full set of optoacoustic signals recorded with minimum distortions using ultrawide-band ultrasonic transducers. The following mathematical processing enables accurate quantitative tomography, fulfilling a longstanding need in medical diagnostics (and specifically, diagnostics of cancer) to measure functional parameters such as [tHb] and [sO2] as well as concentrations of specific protein receptors and other physiologically important molecules:

a. Restore original profiles of optoacoustic signal generated in the tissue ROI by instant laser pulses using deconvolution of acousto-electrical and spatial impulse response functions of ultrawide-band ultrasonic transducer from the detected optoacoustic signals.
   b. Reconstruct 3D optoacoustic tomography images of tissue ROI using rigorous algorithms utilizing complete data sets acquired in full view geometry. To increase the image accuracy even further, iterative methods of optoacoustic tomography can be utilized.
   c. Normalize distribution of incident optical fluence on the surface of tissue ROI by equalizing image brightness of all surface voxels. If the optical absorption coefficient of surface voxels of the ROI is not equal, then perform this step of incident optical fluence normalization using tissue ROI stabilizer. The tissue ROI stabilizer is a spherically or cylindrically shaped thin plastic cup that is placed on tissue ROI to assure that ROI has specific and well-defined shape and dimensions. Such stabilizer made of optically and acoustically transparent plastic significantly increases accuracy of coregistered image reconstruction by avoiding any tissue movement during the scan and providing precise coordinates of the ROI surface. An example of tissue ROI stabilizer is a breast cup shown in FIG. 1D with parameters of the spherical surface selected individually for each patient.
   d. Normalize distribution of the optical fluence through the entire volume of the tissue ROI by compensating for the effective optical attenuation. The FLD subsystem is designed to deliver optical energy orthogonally to the tissue ROI surface along the radius vector connecting each surface voxel with the focal point of the spherical imaging tank or the axis of symmetry of the cylindrical imaging tank. Therefore, compensation of the effective optical attenuation can be performed along these radius vectors, R. Typical effective optical attenuation in biological tissues can be described by the Beer-Lambert law as $\sim\exp(-u_{\mathit{eff}} R)$, where $u_{\mathit{eff}}$ is the effective optical attenuation coefficient at a given laser wavelength, and R is the depth in tissue measured from the surface voxel along the radius vector of light propagation. A more accurate function of the effective optical attenuation can be measured experimentally from the gradually decreasing background voxel brightness on the images reconstructed in step (b). Even though such measurement is not possible in the present state of the art, the QOAT system utilizes ultrawide-band ultrasonic transducers which enable measurements of such low frequency slopes on optoacoustic images as the slope of the effective optical attenuation by biological tissues. After normalization (equalization) of the optical fluence through the volume of tissue ROI, voxel brightness of the image first reconstructed in step (b) becomes proportional to the optical absorption coefficient.

e. Perform signal processing step (a) and image processing steps b, c, d for each of the cycling laser wavelengths selected for the imaging exam.

f. Use coregistered optoacoustic images obtained in step (d) for two or three cycling laser wavelengths to calculate quantitative molecular or functional images.

g. Use complete sets of ultrasound signals to reconstruct images of ultrasound reflection or attenuation or speed of sound and assure their coregistration with molecular (functional) images. Both, optoacoustic and ultrasound images require knowledge of the speed of sound distribution in the tissue ROI. Therefore, images of SoS can be used to enhance accuracy (contrast and resolution) of optoacoustic images and images of ultrasound reflection or attenuation.

h. Display molecular (functional) images overlaid with coregistered anatomical images based on ultrasound reflection, attenuation or speed of sound. These final overlay images display in colors quantitative values of molecular concentrations and functional parameters within anatomical tissue structures displayed by gray scale contrast on ultrasound images.

i. Computer also has an operator interface for communicating commands to the system through a key board or voice using artificial intelligence software.

6. High-resolution screen for image display. The display can be physical (such as LCD, LED) or holographic. The display can have touch screen capability for communicating commands to the computer.

Dual Modality of Molecular-Anatomical Imaging
Limitations of the Present Technologies for the Breast Cancer Care Presently employed x-rays based breast screening and diagnostic imaging modalities of mammography and tomosynthesis have serious limitations of sensitivity and specificity, especially in the dense and heterogeneous breast of younger women. Based on the optimal ratio between risk of exposure to ionizing radiation and benefits of early detection, the American Cancer Society recommends one mammography every two years and only after 50 years of age (14). Breast-ultrasound is, therefore, used as an adjunct to x-ray screening modalities (15). Ultrasound in its 2D and 3D versions is employed as a diagnostic imaging modality due to a very high rate of false positive findings. However, even when both, mammography and ultrasound, suggest cancer and recommend biopsy, the rate of negative biopsy procedures exceeds 70% (16).

Optoacoustic (OA) Functional Imaging

From the very early research in optoacoustic imaging of breast cancer, it was envisioned as a functional imaging of tumor angiogenesis (17). With OA, the main chromophore is hemoglobin, so if the tumor is full of blood, the vasculature and therefore tumor will be more visible. Ultrasound alone can also lead to false-positive diagnoses, which can be downgraded by adjunct optoacoustic imaging (10). In the original study from the previous system, LOUISA, where transducers were larger (2 cm), it bunched vasculatures together. The current system has smaller transducers (1.1 mm), as well as a spherical objective, as opposed to linear in the previous system. In the past tumors were able to be seen with some vasculature, but now tumors and highly articulated vasculature are now able to be seem, indicating a readiness to begin clinical trials.

Functional imaging that separates hemoglobin and oxy-hemoglobin using tissue illumination with at least 2 optical wavelengths in the near infrared spectral range was first demonstrated by Chance (18).

$$THb(\vec{r}) = [Hb](\vec{r}) + [HbO2](\vec{r}) = \frac{\mu_a^{\lambda_1}(\varepsilon_{HbO2}^{\lambda_2} - \varepsilon_{Hb}^{\lambda_2}) - \mu_a^{\lambda_2}(\varepsilon_{HbO2}^{\lambda_1} - \varepsilon_{Hb}^{\lambda_1})}{\varepsilon_{Hb}^{\lambda_1}\varepsilon_{HbO2}^{\lambda_2} - \varepsilon_{Hb}^{\lambda_2}\varepsilon_{HbO2}^{\lambda_1}} \qquad \text{Eq. (1)}$$

$$SO2(\vec{r}) = [HbO2]/\{[Hb](\vec{r}) + [HbO2](\vec{r})\} = \frac{\mu_a^{\lambda_2}\varepsilon_{Hb}^{\lambda_1} - \mu_a^{\lambda_1}\varepsilon_{Hb}^{\lambda_2}}{\mu_a^{\lambda_1}(\varepsilon_{HbO2}^{\lambda_2} - \varepsilon_{Hb}^{\lambda_2}) - \mu_a^{\lambda_2}(\varepsilon_{HbO2}^{\lambda_1} - \varepsilon_{Hb}^{\lambda_1})} \qquad \text{Eq. (2)}$$

Using the same formulas applied to data collected with photoacoustic microscopy, Wang demonstrated functional changes in blood oxygen saturation in a live rat (19). Presently, a number of research groups are developing methods of increasing quantitative accuracy of the functional imaging, especially challenging in volumetric imaging in the depth of tissues (20).

Quantitative Imaging Through Compensation for Optical Fluence Attenuation

The rotating fiberoptic light delivery system of LOUISA is designed to provide as homogeneous integral illumination of the breast as only experimentally possible. On the other hand, it is not possible to avoid optical attenuation of near-infrared light in breast tissues, which results in a spherically symmetric gradient of the effective optical fluence in the breast hemisphere. It is interesting to note that reduced effective optical fluence in the focal point of the breast hemisphere is partially compensated for by enhanced resolution in the focal area of the transducer array. The brightness of microvessels with diameters smaller than the spatial resolution will be lower due to the limited light penetration in tissue, but would be higher due to increased resolution of the system.

In order to reconstruct volumetric images with brightness independent of the depth from the illuminated surface, brightness of voxels is exponentially increased in the radial directions form the skin surface to the focal center of the breast. Ultrawide band ultrasound transducers allow detection of lower ultrasonic frequencies and thus visualize the background absorbed optical energy. This, in turn, allows direct measurements of the effective optical attenuation from each acquired optoacoustic image. The measured effective optical attenuation in the breast of a patient at 757 nm was found to be approximately $u_{eff} \sim 1.15/cm$ and the same number was measured at the wavelength of 800 nm. Therefore, function exp (1.15R) is applied to the brightness palette of the optoacoustic images, where R is the hemisphere radius. This approach was sufficient for reconstruction of functional images of [sO2] showing either oxygenated blood in red or deoxygenated blood in blue.

Coregistration of Functional and Anatomical Images

Even though breast ultrasound has low specificity in breast cancer diagnostics, this modality is quite sensitive and provides a good view of anatomical features which allows for general understanding of breast morphology. Ultrasound can deliver some level of specificity based on the shape of the tumor shadow, i.e., benign tumors have round shape while cancerous lesions have heterogeneous morphology and an "ugly" shape often with sprouts. What is missing in ultrasound is the functional/molecular information, such as density of angiogenesis and blood oxygen saturation, which is specific for differentiation of malignant tumors from benign masses and cysts (21). That is coregistration of optoacoustic and ultrasound images is well justified, especially given that one and the same probe and one and the same electronics can be utilized for both modalities (22-23).

In the earlier study it was demonstrated that tumor morphology visualized in optoacoustic images well resembles the morphology presented in B-mode ultrasound (5). The next step is to display functional parameters of total hemoglobin and blood oxygen saturation within the tumor and its proximity as presented on gray scale ultrasound images. 2D overlay of coregistered optoacoustic and ultrasonic images has been successfully demonstrated in a statistically significant clinical study, which showed a 2-fold increase in the diagnostic specificity of the dual modality compared with ultrasound alone (3).

Full view 3D optoacoustic images and partial view 2D optoacoustic images are acquired at two rapidly cycling laser wavelengths in the near-infrared spectral range. 2D anatomical images of the breast are provided by B-mode ultrasound using an arc shaped probe to achieve a wider acoustic aperture and greater lateral resolution. 3D images of the breast anatomical background is enabled in LOUISA by a sequence of B-mode ultrasound slices acquired with a transducer array rotating around the breast. This creates the possibility to visualize distributions of the total hemoglobin and blood oxygen saturation within specific morphological structures such as tumor angiogenesis microvasculature and larger vasculature in proximity of the tumor.

Challenges of 2D Optoacoustic Tomography

Optoacoustic imaging systems based on hand-held probes of ultrasonic transducers grow in their popularity in the biomedical imaging community. These systems provide two-dimensional images at standard video rates in applications related to detection of cancer and vascular abnormalities. Due to the compact dimensions of hand-held probes, these real-time imaging systems can be useful for guiding needle insertion into the most aggressive part of the tumor during biopsy and for mapping circulation and nerve networks in the course of surgery. On the other hand, hand-held probes have significant limitations associated with their small size and thus small acoustic aperture of the ultrasonic transducer array: (i) providing an incomplete data set making it theoretically impossible to display true brightness/contrast using reconstruction tomography; (ii) poor lateral resolution within the image plane, (iii) poor rejection of out of image plane signals, especially those containing low ultrasonic frequencies emitted by large objects. The backward mode of optoacoustic imaging with laser illumination and ultrasonic detection within the same probe on the same side of the skin, brings in challenging design requirements of hypoechoic probe housing, rejection filters for the scattered laser light illuminating the acoustic lens and overwhelming the ultrasonic transducers. This creates artefact signals and non-zero signal slope that make it very difficult to distinguish relevant signals from the background. Our design of the hand-held probe solved the challenges of the backward mode imaging (8). Because of the advanced probe design and ultrawide-band ultrasonic transducers, the optoacoustic system can achieve higher volumetric contrast of breast tumors and greater imaging depth, which in turn, enabled clinical viability of this system (3). However, 2D system based on a hand-held probe cannot be used for breast screening due to prohibitively long examination time and operator dependence. Thus, 3D automatic full view system should be used for screening in conjunction with 2D system that serves for imaging lymph nodes surrounding breast and potentially receiving drainage of cancer cells from the main breast tumor.

Improvements in LOUISA

All of the above limitations have been alleviated or compensated for in the three-dimensional full view tomography system, LOUISA. The laser illumination is separated in LOUISA from the transducer array, and the optoacoustic probe is combined with the ultrasound probe using 1.5D or 2D array of ultrawide band ultrasonic transducers without an acoustic lens.

Quantitative Tomography System

Full View 3D Optoacoustic System

Many of the limitations of the limited view two-dimensional optoacoustic imaging system can be avoided in the full view three-dimensional system. Previously, advantages of the full view 3D optoacoustic tomography were demonstrated by developing the Laser Optoacoustic Imaging System, LOIS-3D, designed for preclinical research in live mouse models of human disease. LOIS-3D uses an arc-shaped array of 96 ultrawide-band ultrasonic transducers and the subject is rotated 360 deg creating a sphere with 96×360=34,560 virtual detectors (24). The design of LOIS-3D was scaled and enhanced with a number of advanced design features, which resulted in the present design of the QOAT system, LOUISA. These advances include a new hemispherical imaging module rotating around the breast, a 1.5D/2D array of amplified ultrawide-band ultrasonic transducers sensitive to a frequency range of about 50 kHz to about 15 MHz, arc-shaped fiberoptic illumination paddle independently rotating around the breast, and a new dual wavelength pulsed Cr:LICAF laser with two cycling wavelengths of about 757±5 nm and about 850±5 nm. The basic principle schematics of the full view optoacoustic tomography subsystem, the imaging module design, and the system photograph are depicted in FIGS. 1A-1D, which is an upgrade to the preclinical system depicted in FIG. 13.

The imaging module of the breast-scanning system, LOUISA, similarly to the preclinical research system, LOIS-3D, contains a 90 degree arc-shaped array of 96 ultrawideband (50 kHz to 6 MHz) ultrasonic transducers. The noise equivalent pressure NEP~1.5 Pa of these transducers enables deep tissue imaging with high sensitivity. The increased spatial resolution ~0.3 mm of this system is due to three factors, that are (i) high-cutoff frequency of 6 MHz, (ii) 3D idealization of the breast shape into a hemisphere with an optically clear acoustically thin plastic cup-stabilizer, and (ii) illumination of the full breast and integrating all optoacoustic signals for each of the 320 rotational positions of the probe. Alexandrite LASER (Light Age, Somerset, NJ) used in the system emits 50 ns pulses at two cycling wavelengths, 757 nm and 797 nm, separated by either 50 ms or 100 ms time delay, which enables accurate coregistration of the two optoacoustic images and calculation of functional images of [tHb] and [sO2] (25). The laser pulse energy available from this laser is up to 800 mJ, which permits one to achieve an optimal (safe) optical fluence of F-20 mJ/cm$^2$ for breast illumination with the total beam area of 40 cm². Therefore, it takes up to 10 steps to illuminate the entire large breast with the surface area of about 400 cm² (corresponds to a hemisphere with the radius of 8 cm). Taking into account the two wavelengths, and a setting of 10 illumination steps per wavelength for a fully illuminated breast per transducer step, the theoretical minimum time for a two-wavelength, 10 Hz interleaved scan is: 320×10×2×0.1 s=640 s~10.6 minutes per breast. Improvements are currently being tested to achieve a faster clinical scan by increasing the pulse repetition rate to 20 Hz, increasing the number of fiberoptic paddles to 2 and thus reducing the number of illumination steps to 5, which would reduce the time of scan to ~2.5 min.

Rotational Scan Vs Translational Scan

Figure 2A:
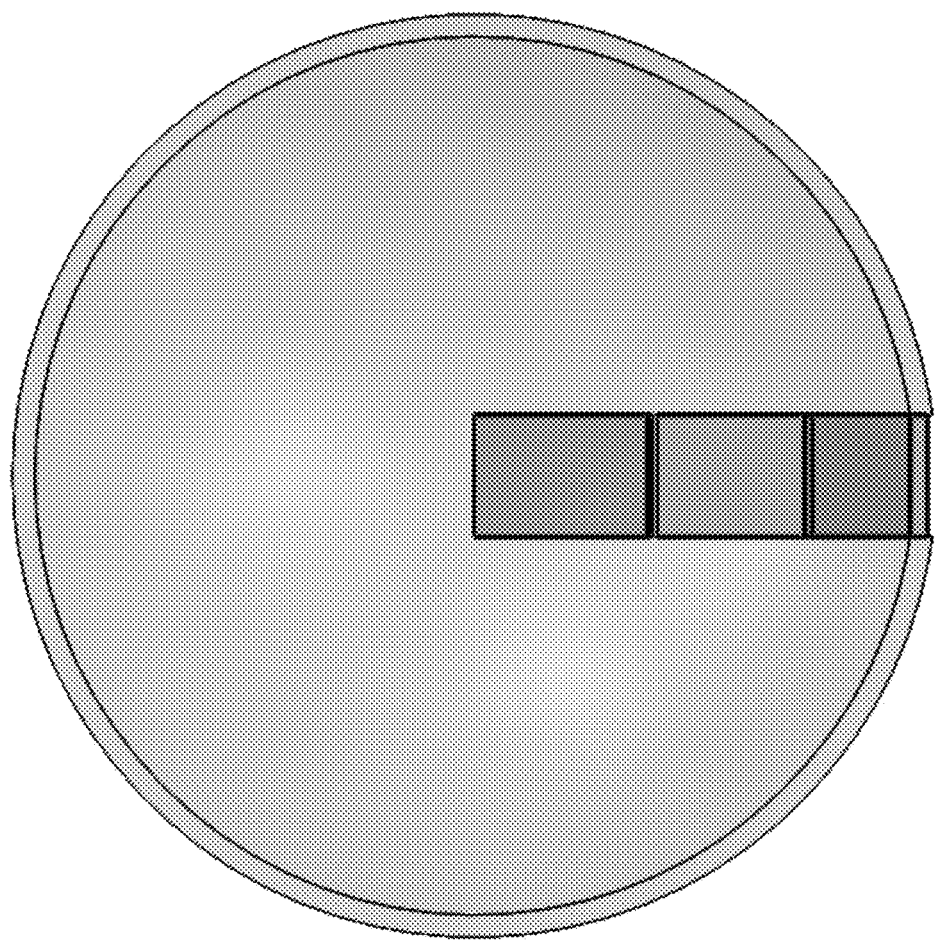
FIGS. 2A-2B are views showing the design of the spherically shaped imaging tank with one arc-shaped probe composed of three flat 2D arrays of ultrawide-band ultrasonic transducers. Each of the three arrays has 1024 transducer elements shaped as 128×8 rectangle (so called 1.5D array), each transducer is made from a stack of piezoelectric composite materials enabling ultrawide band sensitivity when combined with proper backing and front matching layers and coupled into proper electronic preamplifier. The number of the 1.5D arrays in the design depends on the size of the volumetric region of medical interest, so objects smaller than breast even one array will be sufficient. One and the same transducer array serves both purposes of anatomical (ultrasound) and molecular-functional (optoacoustic) imaging. When in static position, the 1.5D array can be used to generate real time (video rate) slices into the depth of tissue. When rotated around the breast the 1.5D array can be used to collect complete set of tomography data and reconstruct full view 3D volumetric images of the breast.
Figure 2B:
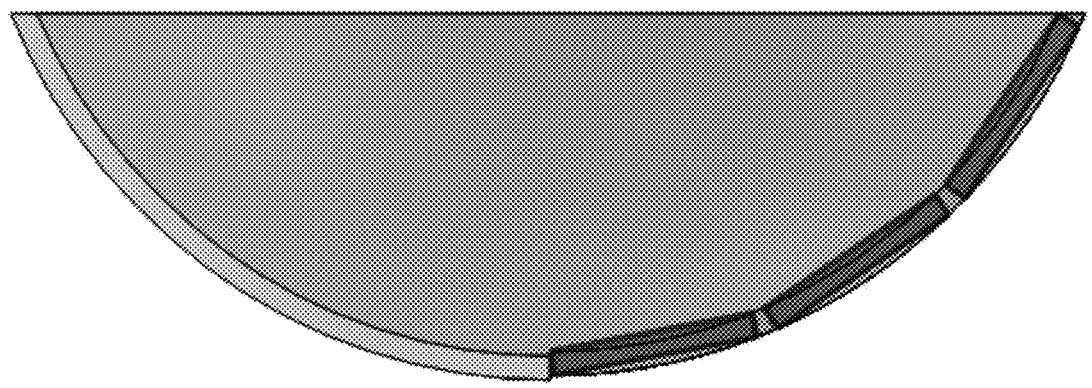

The full view tomography system may be designed to perform a rotational scan and to reconstruct images in spherical coordinates (FIGS. 1A-1D) or, alternatively, it may be designed to perform a translational scan and to reconstruct images in cylindrical coordinates (FIGS. 2A-2B). The advantage of the rotational scan system is that it can acquire a true three-dimensional volumetric image with the spatial 3D resolution equal in all 3 Cartesian directions (x,y,z).

The advantage of the translational scan system is that it uses a full ring of transducers and can acquire and reconstruct 2D images of circular slices with video rate (10-40 Hz) i.e. in real time with physiological events. The translational system has an excellent resolution within a circular 2D (x-y) slice, however, the resolution in the vertical (z-axis) direction that can be obtained by stacking 2D slices into a cylindrical volume is about 2-5 times worse compared with that within the 2D circular slice.

Ultrawide-Band Ultrasonic Transducers

Standard medical ultrasound transducers can detect only within a relatively narrow frequency band and generate electrical reverberations in response to an impulse emitted by biological tissues illuminated with a short laser pulse. This means that the detected optoacoustic signal can be significantly distorted by commercial ultrasound detectors, which in turn limits contrast and resolution of the optoacoustic images. More significantly, intrinsic pressure profiles generated in tissue by short laser pulses can be greatly distorted by the standard transducers which destroys capability of the optoacoustic imaging system to produce true brightness of image voxels and thus disables functional imaging capability. Special efforts were made in the development of ultrawide-band ultrasonic transducers (UBT) for optoacoustic tomography systems.

Figure 3:
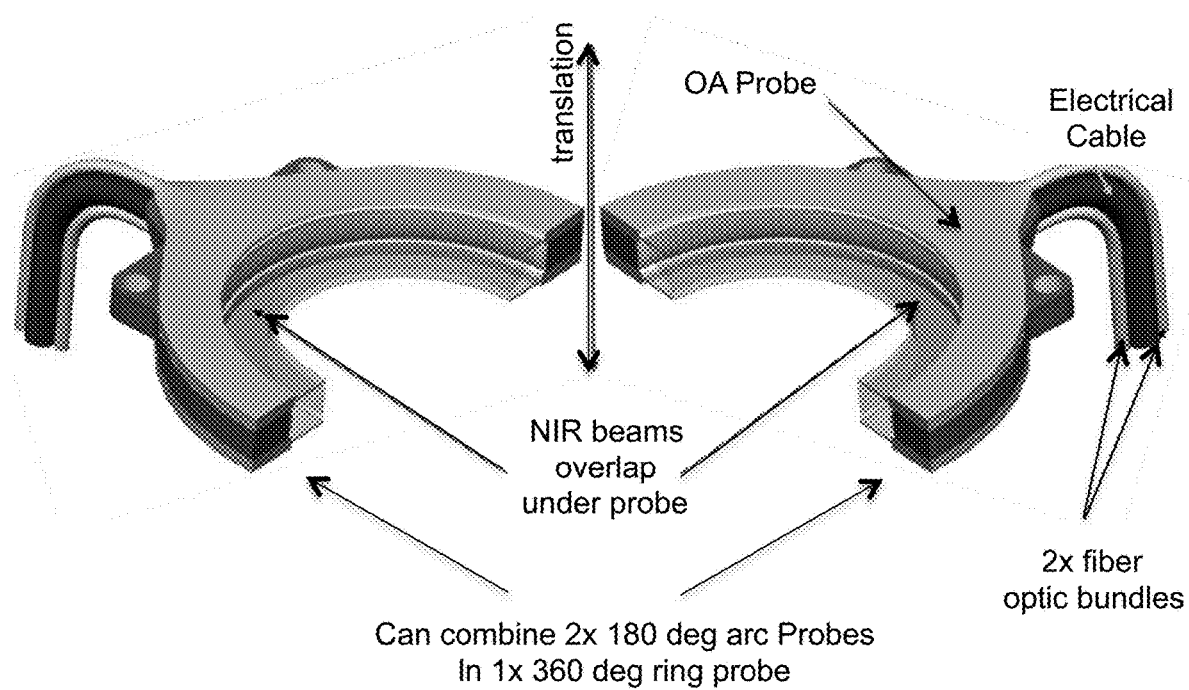
FIG. 3 is a schematic diagram of optoacoustic ultrasonic transducer array for cylindrical 3D tomography system, in which either a half ring or a full ring of optoacoustic transducers with attached fiberoptic illuminators is translated along the z-axis of the cylinder in order to acquire a 3D image. Each of the half-ring arrays has 1024 transducer elements shaped as 256×4 curved rectangle (so called 1.5D array), each transducer is made from a stack of piezoelectric composite materials enabling ultrawide band sensitivity.

Distribution of absorbed optical energy is used to visualize and to characterize quantitatively various tissue structures and their physiological functions based on variations in tissue optical properties. In order to relate tissue structure to optoacoustic images, the acoustic detectors must be able to resolve not only rapid changes in optoacoustic signals associated with sharp edges and boundaries in tissues, but also to reproduce slow changes associated with smooth variation in optical properties within one type of tissue. That is, acoustic detectors must be able to detect both high and low ultrasonic frequencies of acoustic pressure signals. These types of acoustic detectors are called ultrawide-band acoustic transducers (UBT). The best UBT have relatively equal detection sensitivity over the entire ultrasonic range from 20 kHz to 20 MHz, however practical and clinically viable UBT for deep tissue imaging have a bandwidth from about 50 kHz to about 15 MHz. The ultrasonic detection bandwidth of acoustic transducers defines the limits of axial resolution. The lateral resolution of OAT, on the other hand, is defined by dimensions of each acoustic transducer, pitch between two neighboring transducers in the array (or distance between two measurement points in the scanning mode), the total aperture and geometry of the transducer array (measurement surface). To acquire an accurate tomographic image, the object of interest should be surrounded by transducers (FIG. 3), so that all detector positions form a closed surface. Otherwise, reconstruction will be made using an incomplete set of data measurements, which is not quantitatively accurate. Complete sets of temporary resolved optoacoustic data can be acquired using either two-dimensional arrays of transducers, or by one dimensional scanning of a linear array of transducers or by two-dimensional scanning of a single transducer.

Previously, ultrawide-band ultrasonic transducers were developed based on polyvinylidene difluoride (PVDF) copolymers and arrays of these transducers were used for the diagnostic imaging of breast cancer (5). However, due to the low electrical capacitance of PVDF transducers, they could not be made small enough, which limited the spatial resolution in the first prototypes of the breast imaging system. In recent years advances in piezoelectric materials, such as composite material made of single crystal PMN-PT or single crystal PZT piezoelectric ceramics embedded in a polymer matrix or piezoelectric micromachined ultrasonic transducers (pMUT), made it possible to fabricate linear and two-dimensional (1.5D and 2D) arrays of UBTs with high electrical capacitance (~100 pF) and small size (~0.25 mm²). These piezocomposite transducers are sensitive simultaneously in the range of high ultrasonic frequencies to enable high resolution imaging and in the range of low ultrasonic frequencies to enable high contrast optoacoustic imaging of large objects, such as large blood vessels and tumors. While the standard commercial transducers can visualize only boundaries of larger objects in the breast, UBT can visualize volumetric brightness of the larger objects with quantitatively accurate representation of their brightness, thereby enabling acquisition of accurate functional images.

Sensitivity and Depth of Imaging

The acoustic-electrical and spatial impulse responses of the ultrasonic transducers used in LOUISA were measured using previously developed Delta-source of laser ultrasound (26). Also, measurements of optoacoustic signals detected from well-characterized phantoms having spherical inclusions with known optical absorption coefficient, yielded noise equivalent pressure (NEP) of ~1.3 Pa and transducer sensitivity that gives an electrical voltage rise of 16 pV/Pa for NEP. With analog signal amplification of 70 dB the noise amplitude becomes 47 mV as recorded by Analog-to-Digital Converters (ADCs), which is greatly averaged due to addition of signals from 30,720 transducers to each image voxel. With such sensitivity LOUISA can detect relatively large (~1 cm) blood containing objects, such as tumors, with typical optical absorption coefficient of 1/cm illuminated with the effective optical fluence of 0.01 mJ/cm². Such effective optical fluence can be achieved at the depth of Z-50 mm with safe incident laser fluence (27) of 20 mJ/cm² and the effective optical attenuation in the breast of ~exp(−1.15Z) (28).

Examples of the Ultrasound Subsystem

Ultrasound B-mode scan is employed to visualize and ascertain morphological tissue structures.

Rotational Scan System

The ultrasound subsystem for rotational scan is based on a 90 deg arc-shaped array of ultrasonic transducers with a radius of 80 mm, optimized for B-mode breast ultrasound. The array of 192 transducers with the central frequency of 7 MHz with the wide bandwidth of ±3.5 MHz. The ultrasound subsystem provides 2D slices of breast anatomy, which can be readily overlaid with matching optoacoustic slices selected from 3D functional images.

Translational Scan System

The ultrasound subsystem for translational scan is based on either a 180 degree arc-shaped or 360 degree full ring-shaped array of ultrasonic transducers with radius of 80 mm, optimized for B-mode breast ultrasound. The array of 256 (for half ring) or 512 (for full ring) ultrasonic transducers with the central frequency of 5-to-10 MHz with the bandwidth of ±3.5 MHz. The ultrasound subsystem provides 2D slices of breast anatomy, which can be readily overlaid with matching optoacoustic slices. The ring of transducers is being translated to obtained a stack of 2D images comprising a 3D ultrasound tomography image.

The following examples are given for the purpose of illustrating various embodiments of the invention and are not meant to limit the present invention in any fashion.

Example 1

Functional Imaging Validation in Phantoms

The most important advancement of this latest system design compared with previously reported systems is the full breast illumination accomplished for each rotational step of the optoacoustic transducer array using fiberoptic illuminator rotating around the breast independently from rotation of the detector probe. A pilot case study on one healthy volunteer and on patient with a suspicious small lesion in the breast are reported herein. LOUISA visualized deoxygenated veins and oxygenated arteries of a healthy volunteer, indicative of its capability to visualize hypoxic microvasculature in cancerous tumors. A small lesion detected on optoacoustic image of a patient was not visible on ultrasound, potentially indicating high system sensitivity of the optoacoustic subsystem to small but aggressively growing cancerous lesions with high density angiogenesis microvasculature. With safe level of NIR optical fluence, the main breast vasculature (0.5-1 mm) could be made visible at depth of up to 50-mm with 0.3-mm resolution. The results of LOUISA pilot clinical validation demonstrated the system readiness for statistically significant clinical feasibility study.

Cycling two wavelengths of LASER illumination per incremental rotation, it is possible to physically co-register images acquired at these wavelengths with precision of better than 1 voxel (0.2 mm). Distinction between arteries and veins on optoacoustic images, as well as distinction between hypoxic malignant lesions and normally oxygenated benign masses represents valuable functional information to the radiologists in addition to the commonly available breast morphology. The capability of LOUISA to visualize arteries and veins, cancerous and benign tumors is experimentally tested using realistic breast tissue phantoms made of poly(vinyl-chloride)-plastisol, TiO2 powder for optical scattering and plastic coloring dyes for optical absorption (29).

Figure 4A:
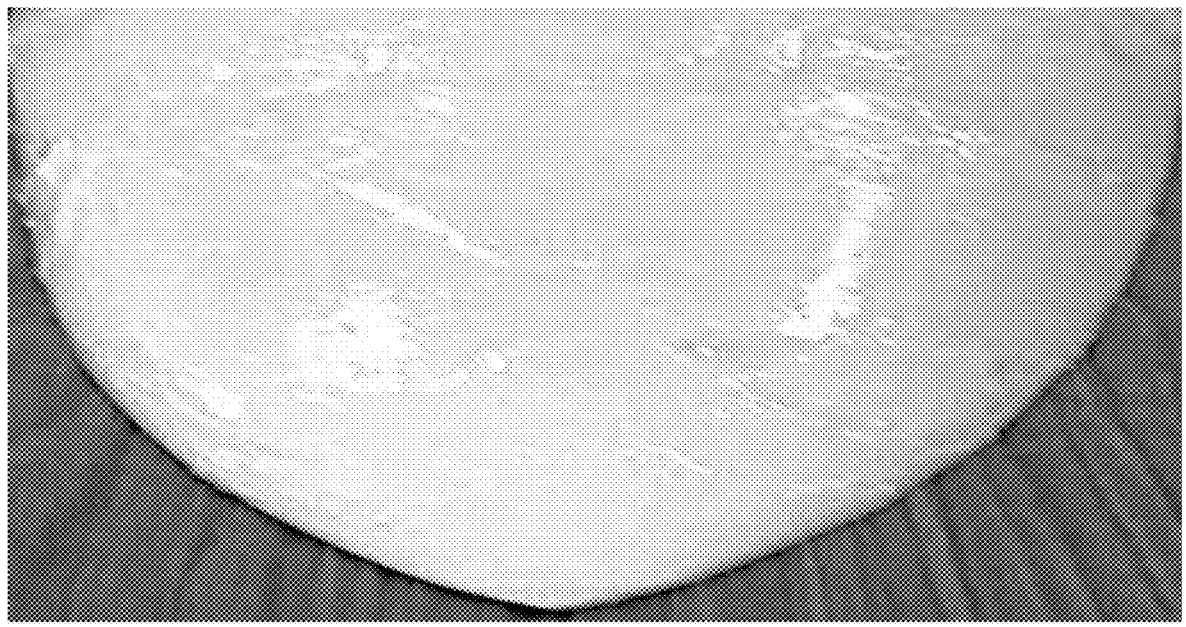
FIGS. 4A-4B are a photograph of a breast phantom made of PVCP with optical properties of an average breast (meff~1.15/cm) (FIG. 4A) and a functional image of [sO2] within the phantom reconstructed from two coregistered optoacoustic images acquired while illuminating the phantom at two cycling wavelengths of 757 nm and 800 nm (FIG. 4B).
Figure 4B:
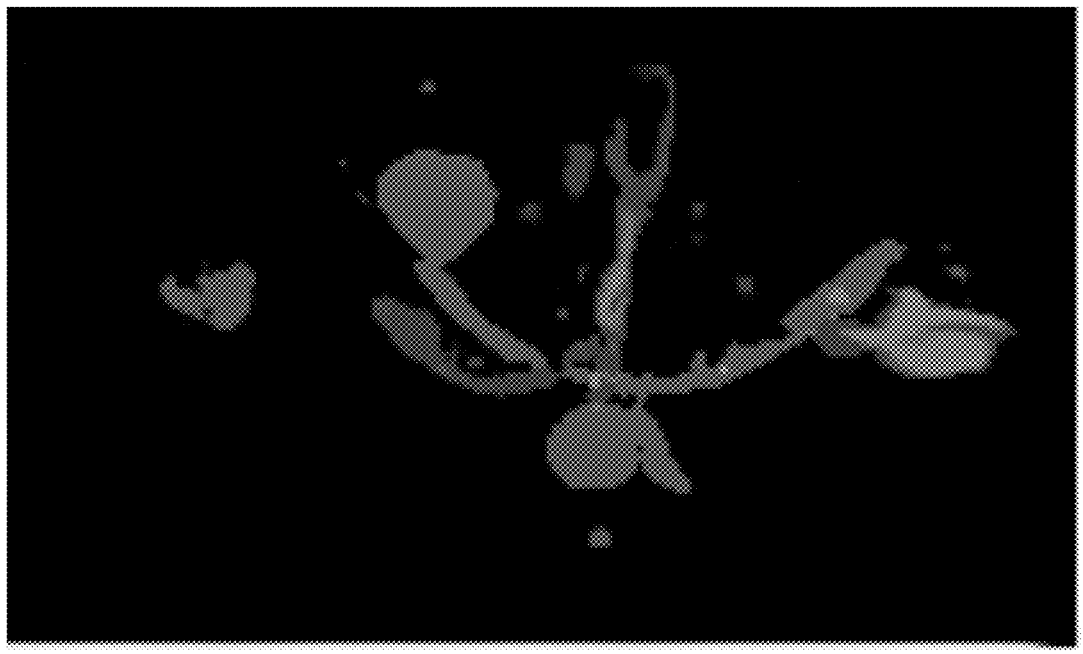
Figure 5A:
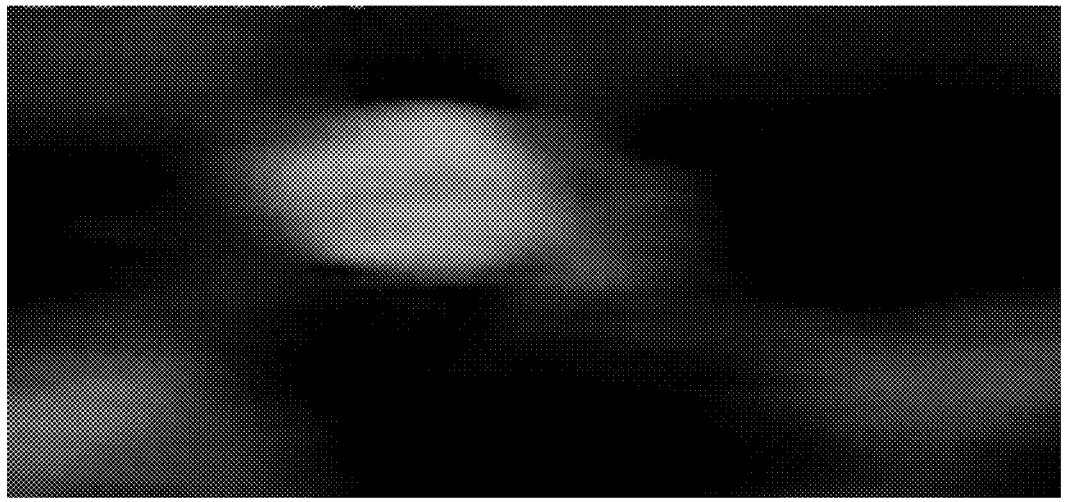
FIGS. 5A-5B are optoacoustic 2D images of an artery/vein pair obtained with a handheld probe of LOUISA.
Figure 5B:
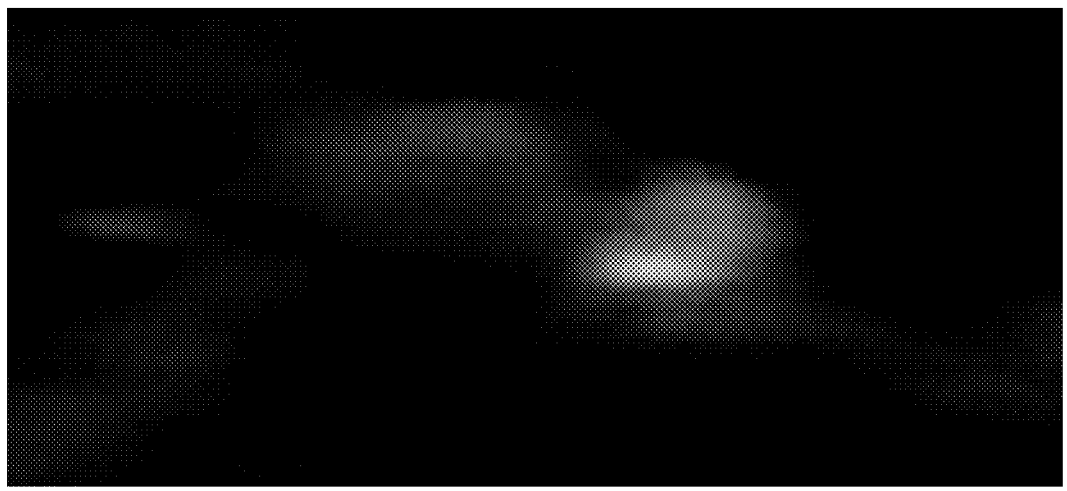

FIGS. 4A-4B show a photograph of the breast phantom and a functional image of blood oxygen saturation, where red color was set for [sO2]>80% and blue color was set for [sO2]<75%. The range between 75% and 80% was made zero (black) brightness. The optical properties of the 6 embedded objects were chosen to represent realistic vasculature and tumors: (1) artery (red) with [sO2]=100%, (2) vein (blue) with [sO2]~70%, benign tumors (red) with [sO2]~95% and [sO2]~85%, aggressive malignant tumor with [sO2]~65% and mixed not aggressive tumor with [sO2]~80%.

The image on FIG. 4B confirms sufficient accuracy of LOUISA3D in functional imaging, given the chosen optical properties of the objects in this phantom. The artery and the vein are well visible and properly colored. Two benign tumors are visible and properly colored. One malignant deeply hypoxic tumor is well visible and properly colored. The second "mixed" tumor with borderline level of blood oxygen saturation is partially invisible and partially colored in red.

Example 2

Clinical Validation of LOUISA

Figures 6A, 6B, 6C:
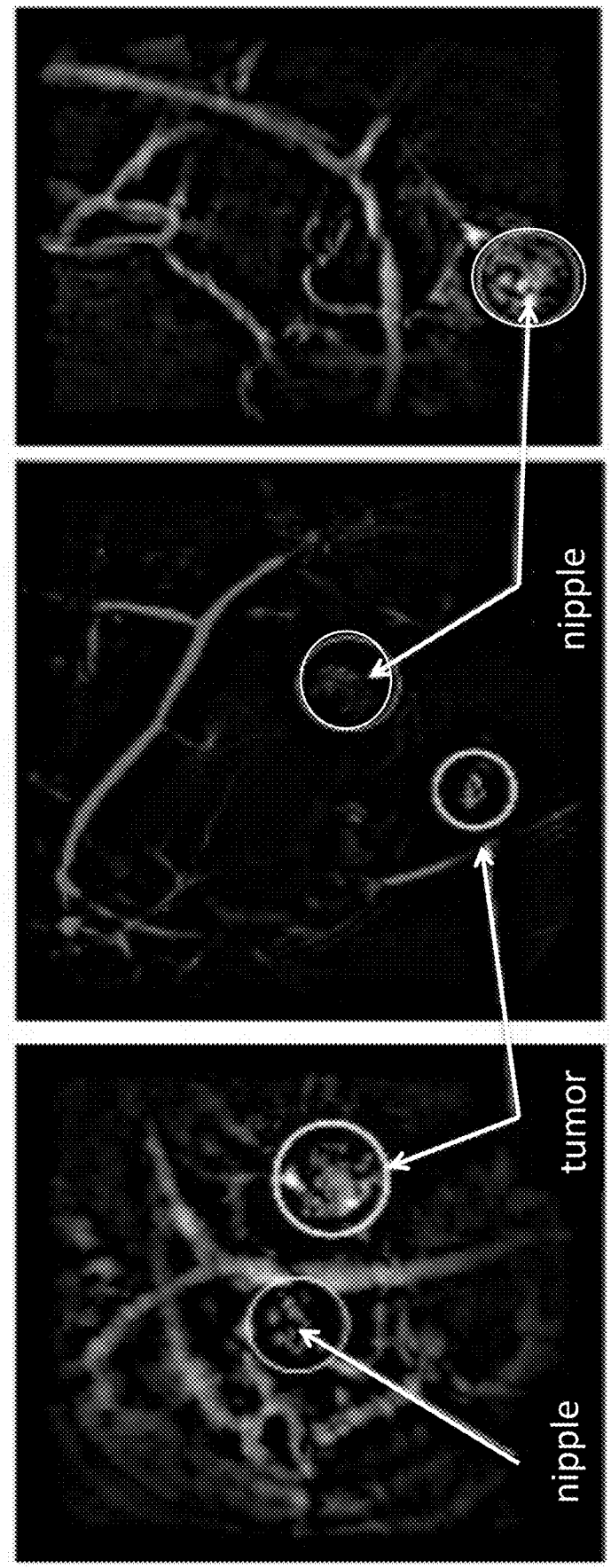
FIGS. 6A-6C are examples of maximum intensity projections (MIP): coronal x-y (FIG. 6A), sagittal x-z (FIG. 6B) and y-z (FIG. 6C) of a 3D optoacoustic images demonstrating LOUISA capabilities to visualize blood vessels, microvessel-filled breast nipple and a small tumorous growth.

The LOUISA system contains a 3D imaging module and a 2D imaging handheld probe. While LOIS-3D, the predecessor of LOUISA, employed a half-time reconstruction algorithm in the spherical coordinates (30), it was necessary to employ full time reconstruction for the hemispherical geometry of 3D image reconstruction in order to retain full view rigorous reconstruction solution for the breast imaging (31). The images of this patient were obtained at a single wavelength of 757 nm, thus blood oxygen saturation of the blood vessels and the tumor was not possible. The nature of a relatively small (3.5 mm) tumor visible in the 2 out of 3 projections (FIGS. 6A-6B, not FIG. 6C) was not conclusively ascertained. FIGS. 6A-6C are a demonstration of LOUISA sensitivity, but not of specificity of tumor differentiation.

A number of improvement in the design of the imaging module and enhancements of the signal processing and image reconstruction algorithms resulted in high-contrast and high-resolution images of the breast showing details of the breast vasculature. The most significant improvement in LOUISA was the invention of the optical fluence normalization (equalization) on the surface of the breast (right under the skin) and the optical fluence normalization through the entire volume of the breast by compensating for the effective optical attenuation at different wavelengths in the laser illumination cycle. The state of the art optoacoustic imaging systems do not have the capability of compensation of the optical fluence as a function of depth in tissue. Instead, these systems use mathematical models of light propagation based on the published average optical properties of the breast, which makes compensation for the effective optical attenuation quite inaccurate, rendering qualitative optoacoustic images, but not quantitatively accurate optoacoustic images. It is our proprietary ultrawide band ultrasonic transducers that possess sensitivity in the lower frequency range that allow direct experimental measurements of the background absorbed optical energy in the breast and then normalization of the effective optical fluence through the depth of tissue, which enables quantitative optoacoustic imaging and ultimately functional and molecular imaging.

Figure 7A:
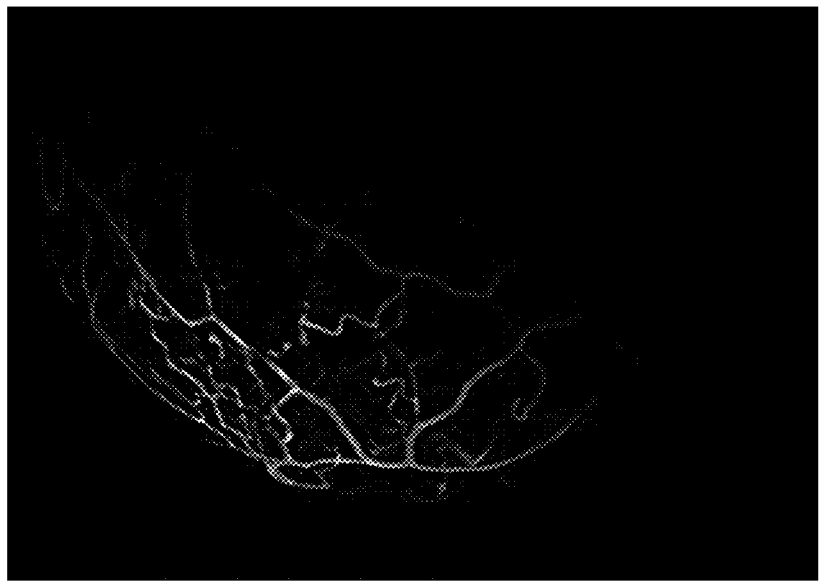
FIGS. 7A-7C are maximum intensity projection (MIP) images of a healthy volunteer breast obtained from a 3D optoacoustic image acquired at the wavelength of 757 nm.
Figure 7B:
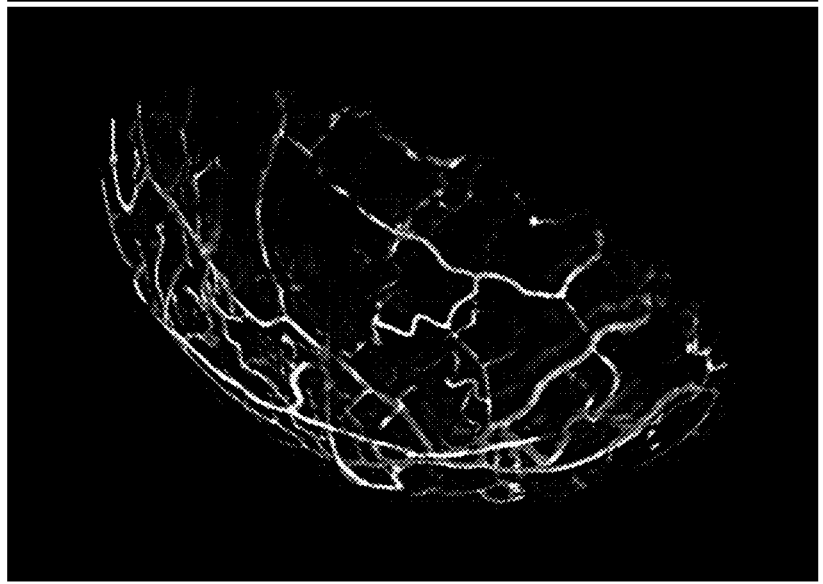

FIG. 7A shows a maximum intensity projection (MIP) of a volumetric optoacoustic image of the normal breast at the wavelength of 757 nm. This is a raw image without any normalization of the optical fluence. Veins are likely dominant vessels on this image, because they have stronger optical absorption at 757 nm wavelength and have larger diameter than arteries. However, even veins are not visible in the depth of the breast due to significant optical attenuation resulting in much lower brightness of the veins in the depth of the breast. FIG. 7B shows the MIP of FIG. 7A after the normalization of the optical fluence on the breast surface.

Figure 7C:
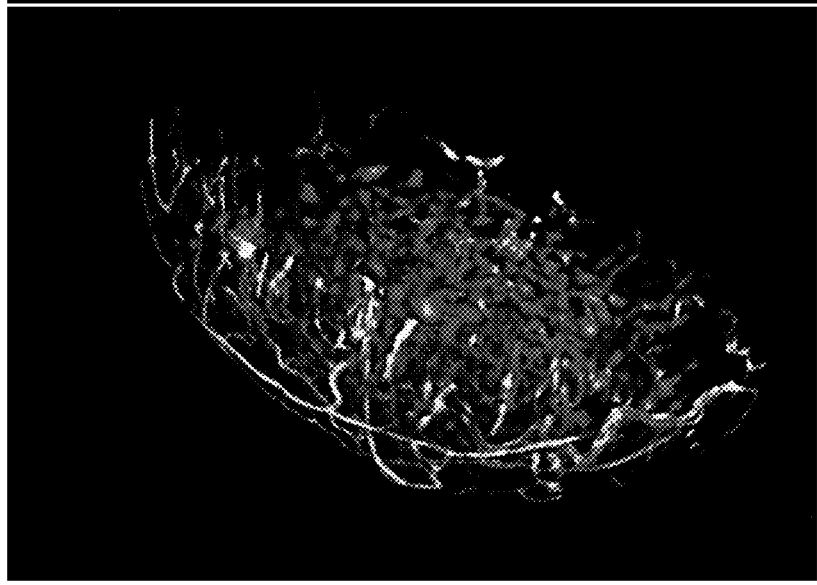
Figure 8A:
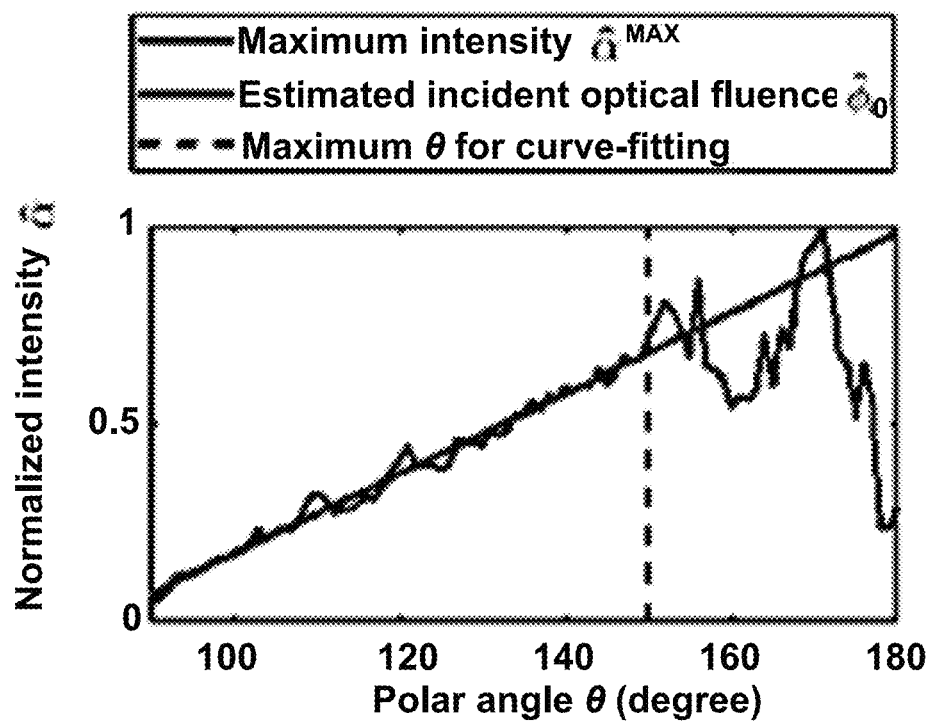
FIG. 8A-8B illustrates the method to normalize the incident optical fluence on the breast surface.
Figure 8B:
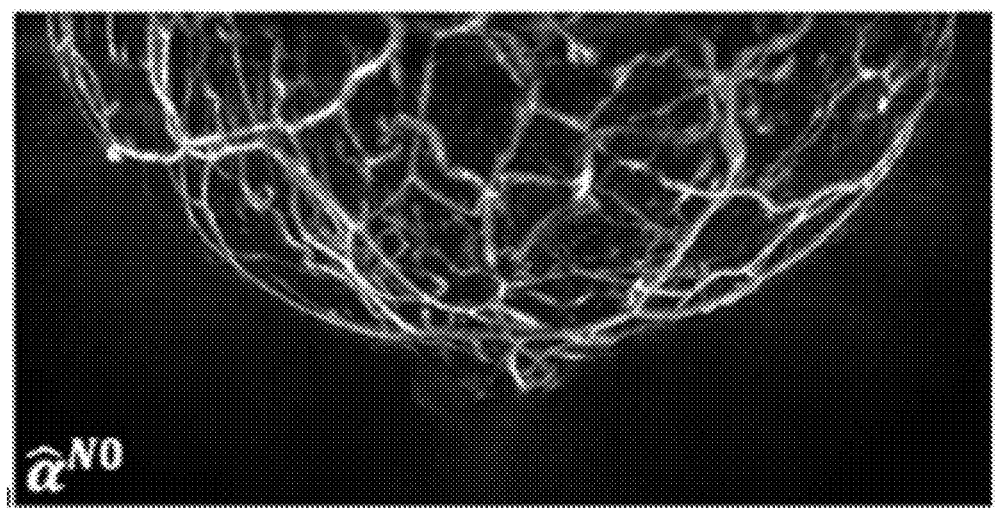

The method for the optical fluence normalization is presented in FIGS. 8A-8B. It was found experimentally that the design of the fiberoptic illumination system produces linear reduction of the total fluence upon rotation around the breast. This happens because at the chest wall the rotation of the fiberoptic bundle makes steps equal to the width of the optical beam. In the area of the nipple the rotating steps do not shift the optical beam, so that the total optical fluence received by this area is larger proportionally to the number of the rotational illumination steps. FIG. 7C shows the MIP of FIG. 7B after the normalization of the optical fluence through the depth of the breast by compensating for the measured effective optical attenuation. The method for the optical fluence normalization as a function of depth is presented in FIGS. 9A-9C. FIG. 7C shows quantitatively accurate 3D optoacoustic image of the breast with vasculature visible through the entire volumetric region of interest and no dependence on the optical fluence.

Figure 10:
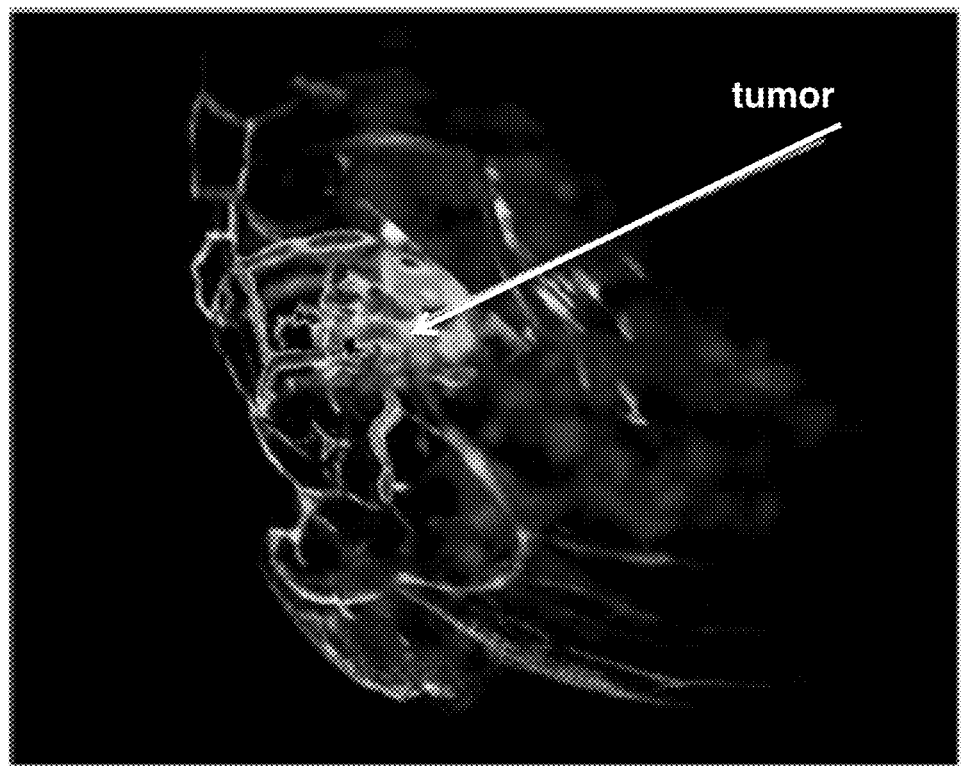
FIG. 10 shows the sum of a 3D optoacoustic image of breast vasculature plus functional image of blood oxygen saturation (sO2) thresholded to display the area with minimum sO2<70%, which matches the location of a breast carcinoma tumor. In order to reconstruct this quantitative functional image, two 3D optoacoustic images were acquired at 757 nm and 1064 nm then were made quantitative by normalization of the optical fluence on the skin surface (see FIGS. 8A-8B) and compensating for the effective optical attenuation through the depth of the breast (see FIGS. 9A-9C).

FIG. 10 shows a clinical 3D optoacoustic image of breast vasculature plus coregistered functional image of blood oxygen saturation (sO2). The brightness of sO2 image was was made zero below threshold to display the area with minimum sO2<70%, which matches the location of a breast carcinoma tumor. The quantitative functional image of sO2 was reconstructed using two coregistered images of the breast acquired at two cycling wavelengths of 757 nm and 1064 nm. The two images were made quantitative by normalization of the optical fluence on the skin surface (FIGS. 8A-8B) and compensating for the effective optical attenuation through the depth of the breast (see FIGS. 9A-9C). The two 3D optoacoustic images were acquired with an array of ultrawide band ultrasonic transducers with sensitivity in the lower frequencies enabling our method of quantitative tomography. FIG. 10 shows potential readiness of LOUISA for feasibility clinical trials in screening and diagnostic imaging of breast cancer.

Figure 11:
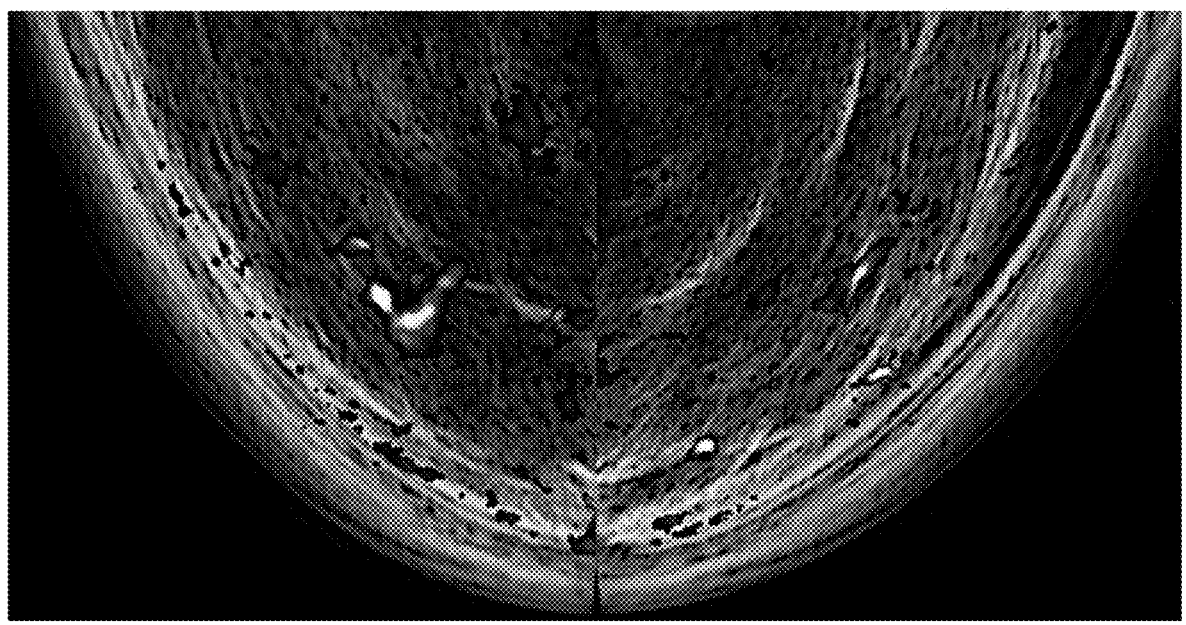
FIG. 11 is an example of a 2D sagittal slice of coregistered and overlaid 3D optoacoustic and ultrasound images. An optoacoustic image slice with an intensity (brightness) threshold to display only maximum brightness superimposed with the corresponding gray scale values of ultrasound image is shown.

FIG. 11 shows an example of the co-registration of OA and US image slices taken through the central axis of the breast hemispherical volume acquired from a healthy volunteer. This type of image that provides information regarding distribution of vasculature will be the most valuable to the radiologist in the presence of a tumor, as the density of vasculature and microvasculature and their geometry in the proximity of the tumor represents diagnostic information. Similarly, functional images of [sO2] and [tHb] can provide differentiation of benign and malignant tumors with especially high specificity when reference to morphology of a tumor and adjacent tissues from coregistered ultrasound image.

Figure 12A:
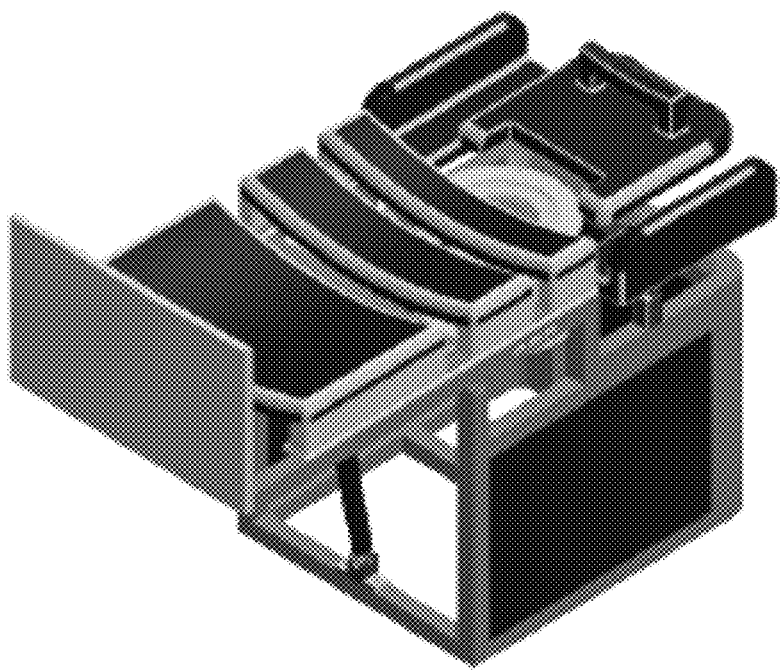
FIGS. 12A-12B show a patient examination platform for the breast imaging system, LOUISA.
Figure 12B:
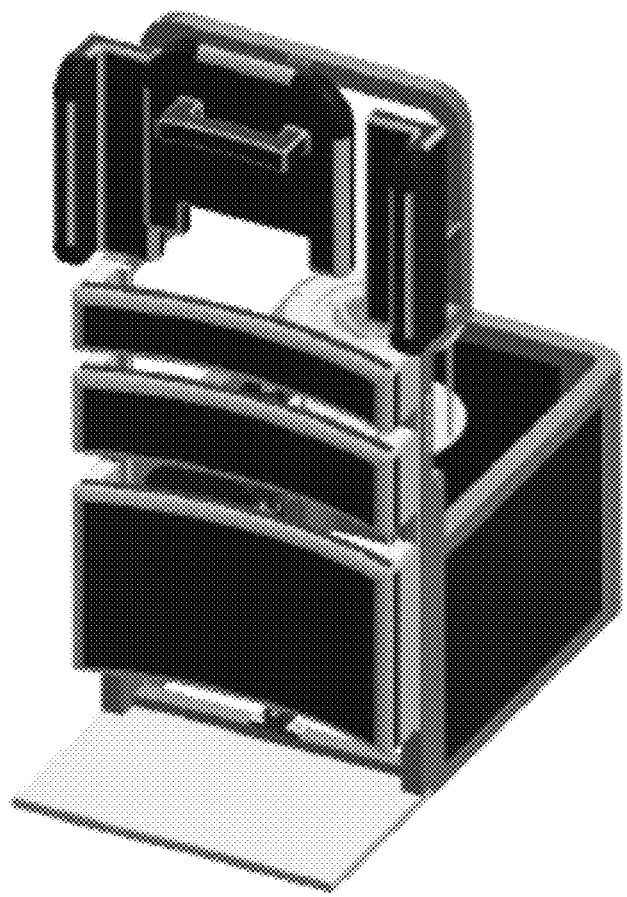

FIG. 12A shows a patient platform, a mechanical improvement through innovation made in LOUISA system for automatic scanning and detection of breast cancer. While the state of the art 3D imaging systems for ultrasound detection of breast cancer are made as an examination bed, we found through clinical testing that this design is inconvenient for the patient, and it takes a long time to properly position of the patient on the examination bed. That is why a new patient platform was invented. A patient approaches this platform, leans on the platform and the platform moves into the horizontal position. FIG. 12B shows the platform in the horizontal position. The patient does not need to move adjusting her position. The imaging module on a 3D translational stage will be brought in an optimal position for the breast exam without any need to adjust the patient position, making the exam comfortable and fast. The improved breast imaging system will be clinically validated. The performance of LOUISA during the validation will make it evident that a number of technical advances make this combined functional and anatomical imaging system a viable solution for the unmet need in breast cancer care.

The following features of LOUISA are important for clinical performance: (i) ultra-wideband ultrasonic transducers sensitive over the frequency range of 50 kHz to 8 MHz; (ii) ultralow noise transducers and electronics with noise equivalent pressure, NEP~1.3 Pa and sensitivity S-0.012 mV/Pa; (iii) full breast illumination/full-view data acquisition that allowed rigorous reconstruction in spherical coordinates; (iv) application of the inverse function of the effective optical attenuation to enable depth independent image brightness. LOUISA represents a hybrid imaging modality with sufficient tumor and blood vessel contrast and adequate resolution of 0.3 mm-0.5 mm in all 3 dimensions (dependent on the breast size). Rapid cycling NIR illumination at 757 nm and 850 nm at 20 Hz allows functional imaging of vasculature and tumors with short scan duration of approximately 2 min, which is acceptable for clinical viability (and much better than 45 min scan of the state of the art MRI system). This short automatic scan is achieved with the "single pulse" illumination in 20 steps of each of the two wavelengths, 45 angular views of 1.5D array (128×8) of our proprietary UBT transducers. The time of image reconstruction is about 5 minutes for over 100 Million voxels and 8192 data samples from each of 46,080 virtual transducers.

The combined 3D optoacoustic and ultrasonic imaging system with spatial coregistration of functional and anatomical information demonstrates clinically sufficient accuracy of quantitative information. LOUISA affords the possibility of automatic examination and screening of an entire breast independent of the operator experience. The clinical application in screening and diagnostic differentiation of breast cancer is expected to be valuable as a replacement for expensive, sensitive but not specific MRI, especially for the dense and heterogeneous breast of younger women.

Example 3

Figure 13A:
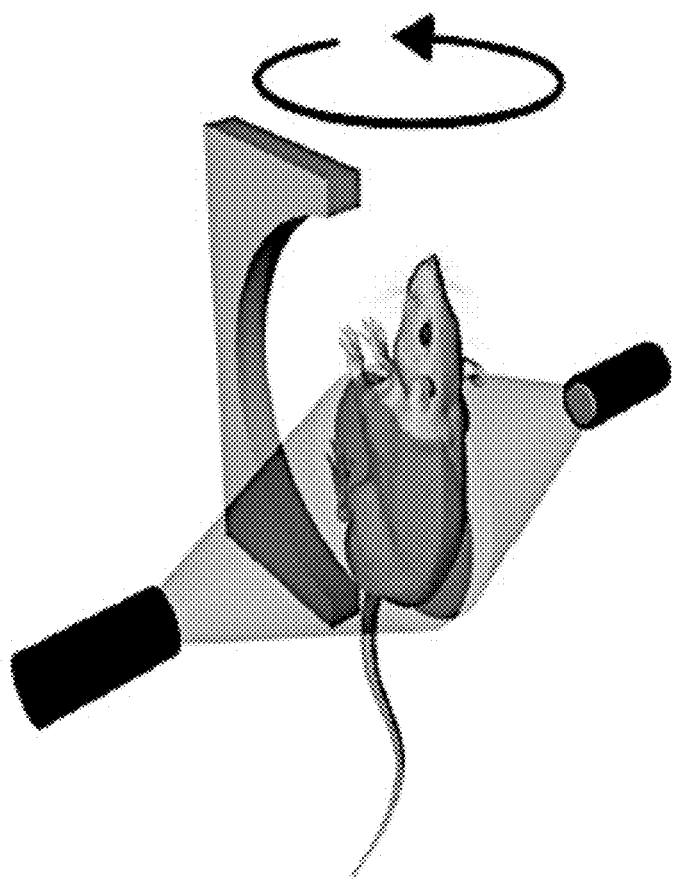
FIG. 13A is a basic cartoon schematic of the full view 3D optoacoustic tomography applied to the imaging of a live mouse.
Figure 13B:
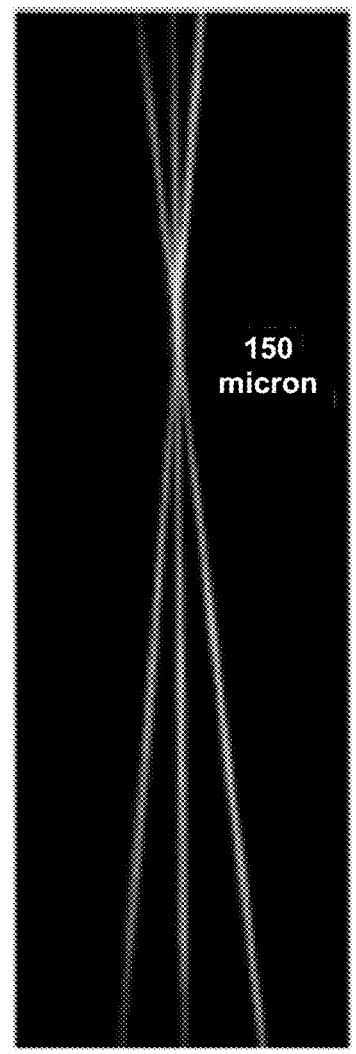
FIG. 13B shows a 3D optoacoustic image of 3 crossed horse hairs with diameter of 150 micron fully resolved on the image obtained with the method presented in FIG. 13A. This figure demonstrates that designs and methods applied to the breast imaging are also applicable to other volumetric regions of interest in clinical and preclinical research.

3D Full View Imaging System for Preclinical Research as an Example of QOAT System Three-dimensional laser optoacoustic ultrasonic imaging system assembly based full-view optoacoustic tomography coregistered with ultrasonic tomography is developed for applications in preclinical research using small laboratory animals, such as a mouse. FIGS. 13A-13B show the basic design and resolution of the mouse imaging system. FIG. 13A shows a basic cartoon schematic of the full view 3D optoacoustic tomography applied to the imaging of a live mouse. FIG. 13B shows a 3D optoacoustic image of 3 crossed horse hairs with diameter of 150 micron fully resolved on the image obtained with the method presented in FIG. 13A. This figure demonstrates that designs and methods applied to the breast imaging are also applicable to other volumetric regions of interest in clinical and preclinical research.

Figure 14:
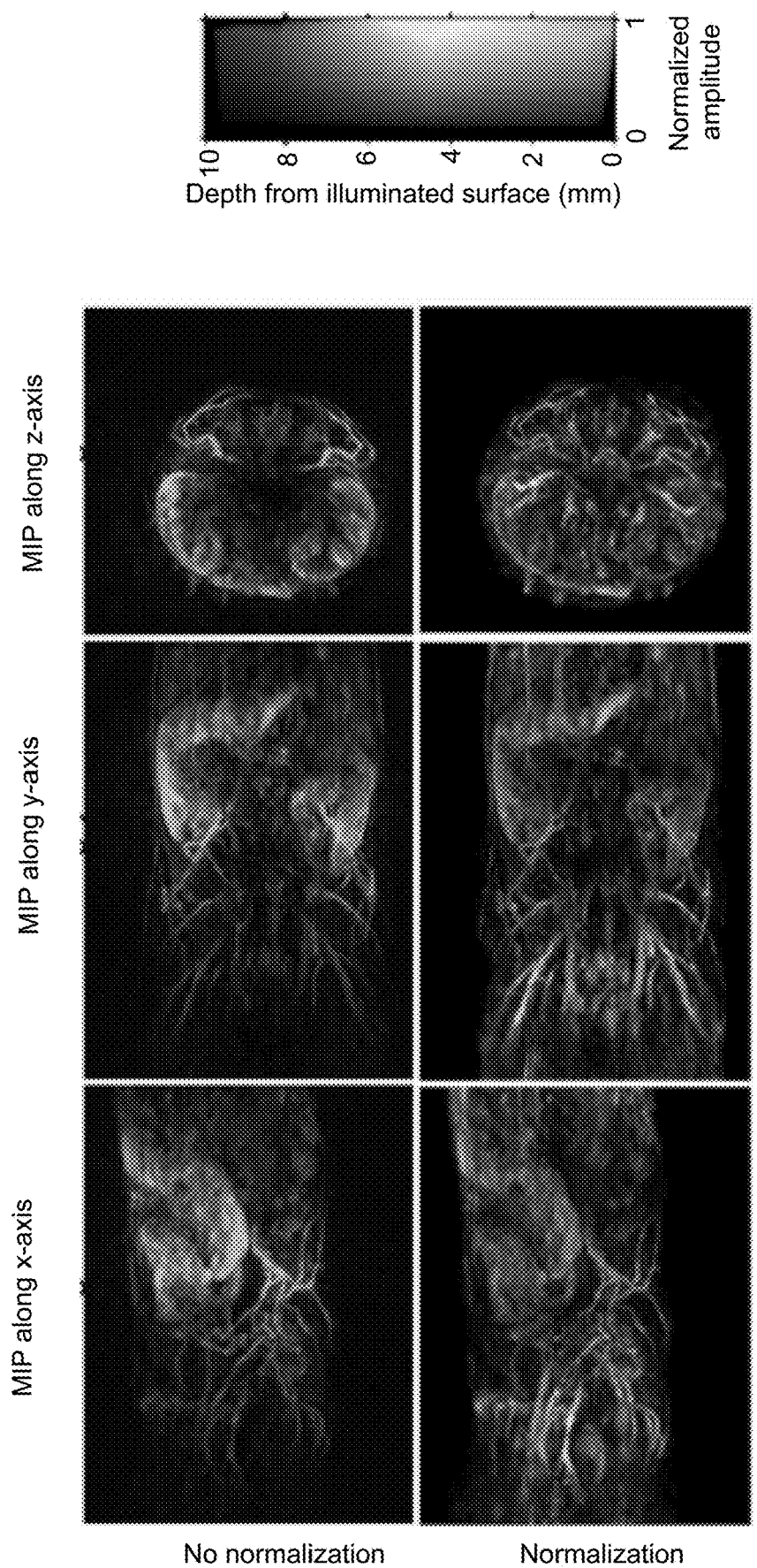
FIG. 14 shows maximum intensity projection (MIP) optoacoustic images of a live mouse body presented along three orthogonal axes: x,y,z. The top 3 images are unprocessed 3D optoacoustic images. The bottom 3 images are processed through normalization of the incident optical fluence on the surface of the mouse and further processed by normalizing the optical fluence through the depth of tissue by compensating for the effective optical attenuation.

FIG. 14 shows maximum intensity projection optoacoustic images of a live mouse body presented along three orthogonal axes: x,y,z. The top 3 images are unprocessed 3D optoacoustic images before optical fluence normalization. The bottom 3 images are processed through normalization of the incident optical fluence on the surface of the mouse and further processed by normalizing the optical fluence through the depth of tissue by compensating for the effective optical attenuation. FIG. 14 (bottom panel of 3 images) shows that mouse vasculature and organs become visible through the entire body after the proprietary fluence normalization.

Successful testing and validation of the mouse imaging machine demonstrates that the invented designs and methods of quantitative tomography are applicable to various types of live subjects and various sizes of the volumetric region of interest.

The following references are cited herein.
1. Folkman, J., New Engl. J. Med., 333:1757-1763, 1995.
2. Savateeva et al., Proc. SPIE, 4618:63-75, 2002.
3. Neuschler et al., Radiology, 285:xxx, 2017.
4. Gartlehner et al., Int J Evid Based Healthc., 11(2):87-93, 2013.
5. Ermilov et al., J Biomed Opt. 14(2):024007 (1-14), 2009.
6. Heijblom et al., Eur Radiol. DOI 10.1007/s00330-016-4240-7dd
7. Kruger et al., Med Phys., 40(11):113301, 2013.
8. Zalev et al., Proc. SPIE, 2013; 8581, 858103.
9. Fakhrejahani et al., PLoS One 2015; 10(10):e0139113, 2015.
10. Toil et al., Scientific Reports, 7:41970, 2017.
11. Deán-Ben et al., J. Biophotonics 9(3):253-259, 2016.
12. Diot et al., Clin Cancer Res., 23(22):6912-6922, 2017.
13. Oraevsky, A. A., "Optoacoustic Tomography: From Fundamentals to Diagnostic Imaging of Breast Cancer", in Biomedical Photonics Handbook, Second Edition: Fundamentals, Devices, and Techniques, ed. by T. Vo-Dinh, CRC Press, Boca Raton, Florida, 2014; vol. PM222, Ch. 21, pp. 715-757.
14. Oeffinger et al., JAMA, 314(15):1599-1614 2015.
15. Gartlehner et al., Int J Evid Based Healthc. 11(2):87-93, 2013.
16. Burkett et al., Acad Radiol. 23(12):1604-1609, 2016.
17. Oraevsky et al., Proc. SPIE, 3597: 352-363, 1999.
18. Liu et al., Phys. Med. Biol., 40:1983-1993, 1995.
19. Wang et al., Nature Biotech., 21(7):803-806, 2003.
20. Deán-Ben et al., J Vis Exp. 2014; 4(93):e51864, 2014.
21. Zhu et al., Radiology; 256(2), 367-378 (2010).
22. Emelianov et al., Proc. SPIE, 5320:101-112, 2004.
23. Niederhauser et al., IEEE Trans. Med. Imaging, 24(4): 436-440, 2005.
24. Brecht et al., J. Biomed. Optics, 14(6):0129061-8, 2009.
25. Klosner et al., Proc. SPIE, 9708:97085B, 2016.
26. Conjusteau et al., Rev. Sci. Inst., 80:093708 (1-5), 2009.
27. American National Standard for Safe Use of Lasers, ANSI Z136.1-2014. Publication by American Laser Institute, New York, N.Y.
28. Taroni et al., Sci Rep. 7:40683, 2017.
29. Spirou et al., Phys. Med. Biol., 50:141-153, 2005.
30. Pan et al., IEEE Transactions on Image Processing, 12:784-795, 2003.
31. Wang et al., Phys Med Biol., 57(17):5399-5423, 2012.

What is claimed is:

1. A laser optoacoustic ultrasonic imaging system assembly (LOUISA) for quantitative tomography, comprising:
   a pulsed laser configured to emit instant pulses of laser light at wavelengths within a red to near-infrared spectral range, said laser operable in a wavelength cycling mode with at least two different wavelengths;
   a fiberoptic bundle that is configured to deliver the instant pulses of laser light to a volumetric tissue region of interest;
   an imaging module comprising:
      an imaging tank shaped to accommodate a shape of the volumetric tissue region of interest;
      at least one optoacoustic array of ultrawide-band ultrasonic transducers configured to detect ultrasonic signals within an ultrawide band of ultrasonic frequencies generated in the volumetric tissue region of interest by the instant pulses of laser light;
      at least one ultrasound array of ultrasonic transducers configured to transmit pulses of ultrasound into the volumetric tissue region of interest and to detect ultrasonic signals reflected from or transmitted through the volumetric tissue region of interest; and
      a coupling medium that fills the imaging tank and through which the instant pulses of laser light and the pulses of ultrasound are transmitted;
   a multichannel electronic data acquisition system comprising analog preamplifiers, analog-to-digital converters and digital data storage, and processing and
   a computer in electronic communication with the multichannel electronic data acquisition system and comprising a multicore central processing unit (CPU) and a multicore graphics processing unit (GPU) and tangibly storing software configured to control said CPU and GPU for system control, said software configured to enable processor-executable instructions for signal processing and image reconstruction and post-processing to produce images of quantitative molecular concentrations or functional parameters within the volumetric tissue region of interest, said instructions configured to:
   a. produce coregistered optoacoustic images acquired using at least two cycling laser wavelengths to obtain quantitative functional or molecular images;
   b. for each image acquired at each wavelength in the cycle, restore original profiles of an optoacoustic signals generated in the volumetric tissue region by the instant laser pulses using deconvolution of acousto-electrical and spatial impulse response functions of the ultrawide-band ultrasonic transducer from the detected optoacoustic signals;
   c. for each image acquired at each wavelength in the cycle, reconstruct 3D optoacoustic tomography images of the volumetric tissue region via rigorous direct algorithms or iterative algorithms utilizing complete data sets acquired in full view geometry;
   d. for each image acquired at each wavelength in the cycle, normalize distribution of incident optical fluence on a surface of the volumetric tissue region by equalizing image brightness of all surface voxels with equal optical absorption;
   e. for each image acquired at each wavelength in the cycle, normalize distribution of the optical fluence as a function of depth through the entire tissue region by measuring an effective optical attenuation from brightness of image voxels and compensating the image for effective optical attenuation via mathematical image processing;
   f. for each image acquired at each wavelength in the cycle, produce and display images of an optical absorption coefficient after normalization of the optical fluence through the volumetric tissue region on optoacoustic images of the absorbed optical energy in the tissue region; and
   g. use all coregistered images acquired at the at least two wavelengths in the cycle to produce a derivative image of quantitative molecular concentrations or functional parameters measured in the volumetric tissue region of interest; and
   a high-resolution display electronically connected to the computer to present the reconstructed images to an operator to display quantitative molecular and functional information within anatomical tissue structures using co-registration of optoacoustic and ultrasonic images.

2. The laser optoacoustic ultrasonic imaging system assembly of claim 1, wherein the red and near-infrared spectral range of wavelengths is about 650 nm to about 1250 nm.

3. The laser optoacoustic ultrasonic imaging system assembly of claim 1, where in the laser is a chromium: lithium calcium hexafluoroaluminate (Cr:LiCAF) laser crystal.

4. The laser optoacoustic ultrasonic imaging system assembly of claim 1, wherein the wavelength cycling mode is two or three wavelengths within the red to near-infrared spectral range.

5. The laser optoacoustic ultrasonic imaging system assembly of claim 4, wherein the two cycling wavelengths are 757 nm and 850 nm.

6. The laser optoacoustic ultrasonic imaging system assembly of claim 4, wherein the three cycling wavelengths are 757 nm, 800 nm and 850 nm or 757 nm, 800 nm and 1064 nm.

7. The laser optoacoustic ultrasonic imaging system assembly of claim 1, wherein the ultrawide-band ultrasonic transducers in the array detect ultrasonic signals within an ultrawide band of 50 kHz to 6 MHz.

8. The laser optoacoustic ultrasonic imaging system assembly of claim 1, wherein the optoacoustic array of ultrawide-band ultrasonic transducers and the ultrasound array of ultrasonic transducers are combined into one array, or the optoacoustic array of ultrawide-band ultrasonic transducers is configured for both optoacoustic imaging and ultrasonic imaging.

9. The laser optoacoustic ultrasonic imaging system assembly of claim 1, wherein the ultrasound array of ultrasonic transducers is a laser ultrasound array comprising polymers with high thermal expansion and filled with strongly optically absorbing materials.

10. The laser optoacoustic ultrasonic imaging system assembly The system of claim 1, wherein the imaging tank in the imaging module has a spherical surface shape or a cylindrical surface shape.

11. The laser optoacoustic ultrasonic imaging system assembly of claim 1, wherein the volumetric tissue region of interest is a human breast, a human head or a small laboratory animal.

12. The laser optoacoustic ultrasonic imaging system assembly of claim 1, said instructions further configured to:
  transmit to the tissue region pulses of ultrasound from the ultrasound array;
  detect with the ultrasound array signals reflected from or transmitted through the tissue region;
  generate speed of sound images based on a distribution of speed of sound within the tissue region;
  generate anatomical images of ultrasound reflection or attenuation from the detected ultrasonic signals;
  coregister the anatomical images of ultrasound reflection, attenuation or speed of sound with quantitative functional or molecular images; and
  display the coregistered images as an overlay of the images of quantitative functional parameters within the anatomical tissue structures or an overlay of the quantitative functional and molecular images and speed of sound images.

13. The laser optoacoustic ultrasonic imaging system assembly of claim 1, wherein the system is a laser optoacoustic ultrasonic imaging system for imaging a breast in a subject, comprising:
  the pulsed laser;
  the fiberoptic bundle that is arc-shaped and configured to rotate around the breast in steps to deliver the instant pulses of laser light at each step to the breast;
  the imaging tank with a spherical surface shape corresponding to the breast;
  the at least one optoacoustic array of ultrawide-band ultrasonic transducers, wherein said optoacoustic array is an arc-shaped 1.5D or 2D array that is configured to detect ultrasonic signals within an ultrawide band of at least 50 KHz to at least 6 MHz generated in the breast by the instant pulses of laser light;
  the at least one ultrasound array of ultrasonic transducers, wherein said ultrasound array is an arc-shaped 1.5D or 2D array that is configured to transmit pulses of ultrasound into the breast and to detect ultrasonic signals reflected from or transmitted through the breast, said ultrasound array optionally combined with the optoacoustic 1.5D or 2D array in one housing or is one array with the optoacoustic 1.5D or 2D array;
  the coupling medium that is optically and acoustically transparent; and
  in an electronic subsystem
    the multichannel electronic data acquisition system;
    the computer in electronic communication with the multichannel electronic data acquisition system;
    the software tangibly stored on the computer and configured to enable the processor-executable instructions; and
    the high-resolution display electronically connected to the computer.

14. The laser optoacoustic ultrasonic imaging system assembly of claim 13, wherein the pulsed laser is operable at two cycling wavelengths of 757±5 nm and 850±10 nm.

15. The laser optoacoustic ultrasonic imaging system assembly of claim 13, wherein the pulsed laser is operable at three cycling wavelengths of 757±5 nm, 800±5 nm and 850±10 nm or 757±5 nm, 800±5 nm and 1064±10 nm.

16. The laser optoacoustic ultrasonic imaging system assembly of claim 13, wherein the optoacoustic array of ultrawide ultrasonic transducers and the ultrasound array of ultrasonic transducers are combined into one array.

17. The laser optoacoustic ultrasonic imaging system assembly of claim 13, wherein the fiberoptic bundle, the optoacoustic array and the ultrasound array are configured to independently rotate around the breast for illumination of the entire breast for each position of the optoacoustic array and the ultrasound array.

18. The laser optoacoustic ultrasonic imaging system assembly of claim 13, wherein a patient examination is made on a platform that moves from a vertical position to a horizontal position, and an imaging module is placed on a computer controlled three-dimensional translation stage, enabling a patient breast scan without patient movement on the platform.

19. The laser optoacoustic ultrasonic imaging system assembly of claim 1, wherein the fiberoptic bundle comprises a hot-fused input tip for maximum optical transmission and an output to enable beam homogeneity on a surface of the volumetric tissue region of interest.

20. A method for imaging quantitative or functional parameters in a volumetric tissue region of interest in a subject with enhanced resolution and accuracy using image of the speed of sound, comprising the steps of:

placing the volumetric tissue region in the imaging tank of the LOUISA system of claim 1;

generating images of quantitative functional parameters or molecular parameters from the coregistered optoacoustic images;

acquiring images of speed of sound distribution within the tissue region;

using images of the speed of sound to improve contrast and resolution of coregistered optoacoustic images or quantitative functional and molecular images; and displaying the generated images with enhanced resolution and quantitative accuracy.

21. The method of claim 20, further comprising:

enhancing the resolution of ultrasound reflection or attenuation images using maps of the speed of sound images.

22. The method of claim 20, further comprising:

detecting at least one cancerous tumor and differentiating it from a noncancerous tumor using coregistered images of the quantitative functional parameters or the molecular parameters displayed within anatomical structures in the overlay of optoacoustic and ultrasonic images.

23. The method of claim 22, wherein the cancerous tumor is a cancerous breast tumor.

24. The method of claim 20, wherein acquiring ultrasound images occurs between acquiring optoacoustic images at cycling wavelengths.

25. The method of claim 20, wherein the quantitative functional parameter comprises a concentration of a protein, of a protein receptor or of a molecule associated with a cancer or a combination thereof.

26. The method of claim 20, wherein the functional parameter is total hemoglobin [tHb] or blood oxygen saturation [sO2] or a combination thereof.

* * * * *